US010092518B2

United States Patent
Daneshvari

(10) Patent No.: US 10,092,518 B2
(45) Date of Patent: Oct. 9, 2018

(54) WET GRANULATION PROCESS AND GRANULATE MATERIAL COMPRISING ARABIC GUM

(71) Applicant: ALPINIA LAUDANUM INSTITUTE OF PHYTOPHARMACEUTICAL SCIENCES AG, Walenstadt (CH)

(72) Inventor: Dana Daneshvari, Rüschlikon (CH)

(73) Assignee: ALPINA LAUDANUM INSTITUTE OF PHYTOPHARMACEUTICAL SCIENCES AG (CH)

( * ) Notice: Subject to any disclaimer, the term of this patent is extended or adjusted under 35 U.S.C. 154(b) by 354 days.

(21) Appl. No.: 14/391,543

(22) PCT Filed: Apr. 10, 2013

(86) PCT No.: PCT/EP2013/001055
§ 371 (c)(1),
(2) Date: Oct. 9, 2014

(87) PCT Pub. No.: WO2013/152852
PCT Pub. Date: Oct. 17, 2013

(65) Prior Publication Data
US 2015/0147405 A1 May 28, 2015

(30) Foreign Application Priority Data

Apr. 10, 2012 (EP) .................................... 12002533

(51) Int. Cl.
*A61K 9/16* (2006.01)
*A61K 36/22* (2006.01)
(Continued)

(52) U.S. Cl.
CPC ............ *A61K 9/1694* (2013.01); *A23L 29/25* (2016.08); *A23L 33/16* (2016.08); *A23P 10/20* (2016.08); *A61K 36/22* (2013.01); *A23V 2002/00* (2013.01)

(58) Field of Classification Search
None
See application file for complete search history.

(56) References Cited

U.S. PATENT DOCUMENTS 3,672,945 A 6/1972 Taylor
5,609,897 A 3/1997 Chandler et al.
(Continued)

FOREIGN PATENT DOCUMENTS

EP 1417958 A1 5/2004
EP 1505078 2/2005
(Continued)

OTHER PUBLICATIONS

International Search Report for PCT/EP2013/001055 dated Jun. 4, 2013.

*Primary Examiner* — Jianfeng Song
(74) *Attorney, Agent, or Firm* — Drinker Biddle & Reath LLP

(57) ABSTRACT

The invention relates to a wet granulation process comprising contacting a material to be granulated with a granulating liquid, wherein the granulating liquid comprises Arabic gum. The process may be used for improving dissolution kinetics of the material to the granulated, for example, of Arabic gum and/or metal salts, such as organic metal salts. Furthermore, the invention relates to a granulate material comprising Arabic gum, wherein the individual granules making up the granulate material are porous, preferably exhibiting a mean porosity of between about 15% to about 75%, which are obtainable by the process according to the present invention. The invention also provides a composition comprising the granulate material, for example, for the preparation of a liquid, such as a beverage, and the granulate material and the composition of the present invention for use as a medicament and/or as a dietary supplement.

10 Claims, 17 Drawing Sheets

Figure 1:
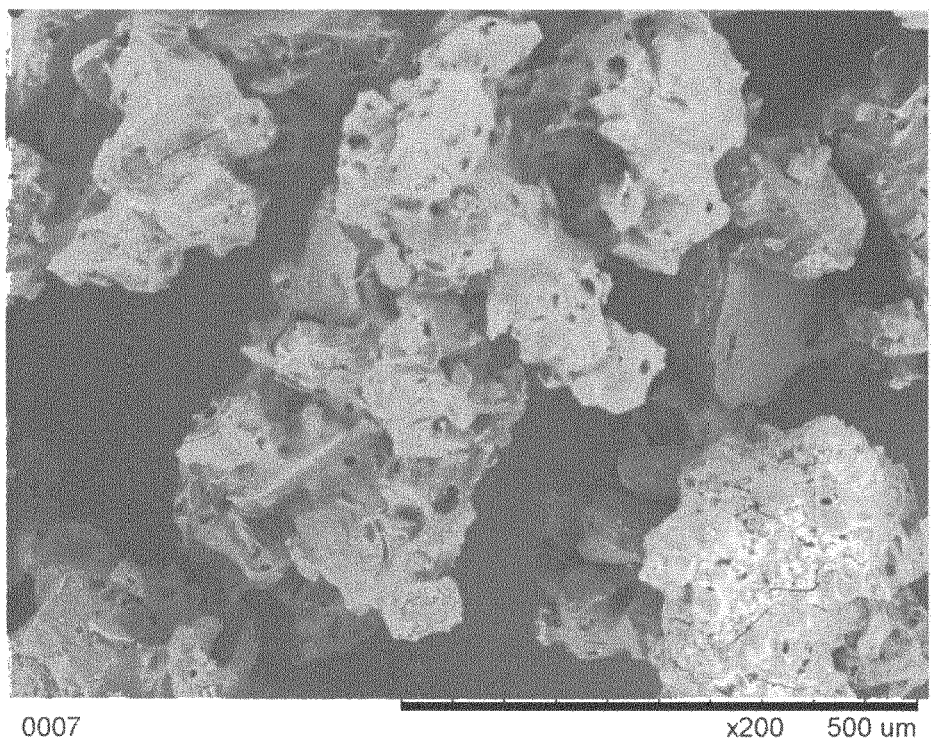
Figure 1:
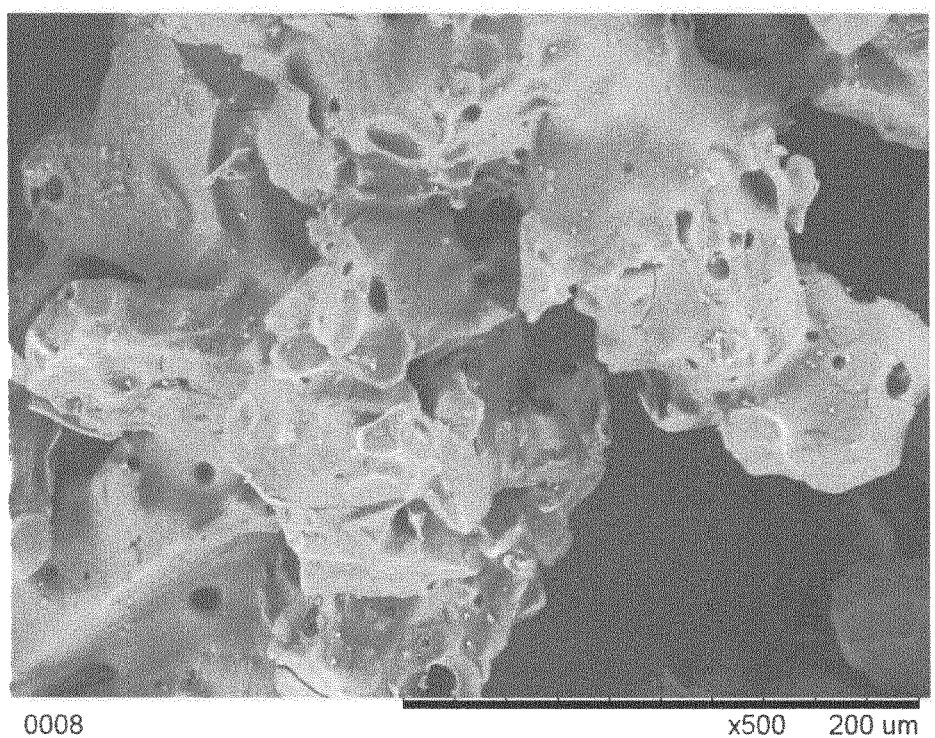

(51) Int. Cl.
　　　*A23P 10/20*　　(2016.01)
　　　*A23L 29/25*　　(2016.01)
　　　*A23L 33/16*　　(2016.01)

(56) References Cited

U.S. PATENT DOCUMENTS

| | | | |
|---|---|---|---|
| 6,858,725 B1 | 2/2005 | Vladyka, Jr. et al. | |
| 7,807,125 B2 * | 10/2010 | Lang et al. | 423/430 |
| 2005/0202084 A1 * | 9/2005 | Adusumilli | A61K 9/0056 |
| | | | 424/464 |
| 2009/0311317 A1 * | 12/2009 | Cherukuri et al. | 424/456 |
| 2011/0052779 A1 * | 3/2011 | Hirata et al. | 426/590 |

FOREIGN PATENT DOCUMENTS

| | | | |
|---|---|---|---|
| KR | 20120029810 A | | 3/2012 |
| WO | WO-9932612 A1 | | 7/1999 |
| WO | WO-2004032901 A1 | | 4/2004 |
| WO | WO-2004047974 A1 | | 6/2004 |
| WO | WO-2004099361 A1 | | 11/2004 |
| WO | WO-2005-011666 | * | 2/2005 |
| WO | WO-2007062723 A1 | | 6/2007 |
| WO | WO-2007065441 A1 | | 6/2007 |
| WO | WO-07094486 A1 | | 8/2007 |

\* cited by examiner

Ca-Lactate Arabic Gum granulate material

Ca-Glutamate Arabic Gum granulate material

Mg-Lactate Arabic Gum granulate material

Zn-Gluconate Arabic Gum granulate material

Multi 1/5 Arabic gum granulate material (Mg-lactate, Ca-gluceptate, Zn-gluconate)

Multi 1/3 Arabic gum granulate material (Mg-lactate, Ca-gluceptate, Zn-gluconate)

|  | Example 1 | Example 2 | Example 3 | Example 4 | Example 5a | Example 5b | Example 5c |
|---|---|---|---|---|---|---|---|
| Orifice (cm) | 1.5 | 1.5 | 1.5 | 1.5 | 1.5 | 1.5 | 1.5 |
| weight (g) | 99.9 | 99.70 | 97.80 | 98.9 | 99.6 | 98.95 | 100.10 |
| Time (sec.) | 13.40 | 9.51 | 8.43 | 10.22 | No Flow | No Flow | No flow |
| Speed (g/s) | 7.45 | 10.48 | 11.60 | 9.68 | N/A | N/A | N/A |
| weight (g) | 99.3 | 99.5 | 99.50 | 100.0 | 99.8 | 99.86 | 100.22 |
| Time (sec.) | 13.34 | 9.53 | 8.57 | 10.38 | No Flow | No Flow | No flow |
| Speed (g/s) | 7.44 | 10.44 | 11.61 | 9.63 | N/A | N/A | N/A |
| weight (g) | 100.0 | 99.1 | 99.90 | 99.9 | 99.8 | 100.13 | 99.98 |
| Time (sec.) | 13.28 | 9.48 | 8.59 | 10.36 | NO Flow | No Flow | No flow |
| Speed (g/s) | 7.53 | 10.45 | 11.63 | 9.64 | N/A | N/A | N/A |
| Φ speed (g/s) | 7.47 | 10.46 | 11.61 | 9.65 | N/A | N/A | N/A |
| σ (g/s) | 0.02 | 0.02 | 0.01 | 0.02 | N/A | N/A | N/A |

Fig. 10

WET GRANULATION PROCESS AND GRANULATE MATERIAL COMPRISING ARABIC GUM

CROSS-REFERENCE TO RELATED APPLICATIONS

This application is a national stage application (under 35 U.S.C. § 371) of PCT/EP2013/001055, filed Apr. 10, 2013, which claims benefit of European Application No. 12002533.3, filed Apr. 10, 2012, both of which are incorporated herein by reference in their entirety.

FIELD OF THE INVENTION

The present invention relates to a wet granulation process for producing granulate material comprising Arabic gum and such granulate material which exhibits improved go solubility characteristics.

BACKGROUND OF THE INVENTION

Arabic gum, also known as gum Arabic, acacia gum, chaar gund, char goond, or meska, is a natural gum made of hardened sap taken from acacia trees. Arabic gum, which is edible and exhibits glue-like characteristics, essentially consists of a branched long-chain polysaccharide (made up of L-arabinose, D-galactose, L-rhamnose and D-glucuronic acid) and alkaline earth metal and alkali metal salts. Arabic gum is primarily used in the food industry, e.g. as stabilizer, emulsifying or thickening agent, and is an important ingredient, for example, in soft drink syrups and "hard" gummy candies such as gumdrops or marshmallows. Furthermore, it is used as a binder, emulsifying or viscosity increasing agent in pharmaceutical and cosmetic compositions. It is also a key ingredient in traditional lithography and is used in printing, paint production (e.g. as binder in watercolor paint), glue (e.g. on postage stamps, envelopes and cigarette papers), and various industrial applications, including viscosity control in inks and in textile industries. It is an important ingredient in shoe polish and is used as a binder in pyrotechnique compositions.

As a raw material, Arabic gum is available in the form of odorless, brittle, dried sap chunks, which have a colorless to brown appearance. For easy handling and processing, e.g. in the food or pharmaceutical industry, as well as for advantageous storage characteristics, the raw material is generally further processed into powder form.

Although Arabic gum provides excellent properties as emulsifying agent, a drawback is its relatively slow dissolution kinetics in aqueous solvents. Satisfactory dissolution of Arabic gum or compositions containing Arabic gum in aqueous solvents, such as water, may require heating and/or vigorous stirring or shaking over a long period of time, and still, floating undissolved Arabic gum material may be observed. The relatively slow dissolution kinetics of available Arabic gum forms complicates handling and processing of Arabic gum materials. For example, food supplements, such as minerals or organic metal salts, are often provided as ready-to-use powdered dosage forms comprising Arabic gum as matrix material. Such powdered dosage forms are generally dissolved in aqueous solvents, such as in water, and are consumed as beverage. For convenient handling of such compositions, rapid dissolution without the necessity of heating or vigorous agitation is desired, since incomplete dissolution may lead to incomplete uptake of effective agents.

There have been some attempts to modify the properties of Arabic gum, in particular, for enhancing the emulsifying ability of Arabic gum. For example, EP 1 505 078 suggests a heat treatment, wherein Arabic gum is heated to not less than 60° C. in an atmosphere having a relative humidity of 30-100% for modifying the emulsifying properties of Arabic gum. However, said method is not suitable for significantly improving dissolution kinetics of Arabic gum in aqueous solvents.

In the pharmaceutical industry, Arabic gum is, for example, used in the production of nutritional supplements. For example, WO 07/094486 discloses a composition for mediating an improved calcium absorption comprising Arabic gum. Administration of such composition aims at maintaining a balanced level of blood calcium which is essential for cardiac function and prevention of cardiovascular disorders, such as atherosclerosis, coronary artery disease, ischemic heart disease, hyperlipidemia and hypertension. Furthermore, WO 2007/062725 discloses biopolymer-stabilized nanoparticles comprising calcium and optionally Arabic gum as a food product. WO 2004/032901 discloses a pharmaceutical excipient comprising inorganic particles in association with an organic polymeric material which may comprise calcium salts and Arabic gum. The nanoparticles described in WO 2007/062723 and the pharmaceutical excipient described in WO 2004/032901 are manufactured by precipitation and/or controlled crystallization methods, such as by calcium phosphate precipitation. According to WO 2007/062723, the particles described therein exhibit low solubility. WO 2007/065441 describes a granulation process of calcium containing compounds with a water-soluble polymeric substance for obtaining granules which are particularly suitable for the preparation of tablets exhibiting high drug load. However, the dissolution rate of the obtained material is low. Finally, U.S. Pat. No. 5,609,897 describes beverage concentrates comprising calcium, vitamin D, a stabilizing gum such as Arabic gum, and vegetable oil. Arabic gum is used as an emulsion stabilizer in the liquid concentrates. Concentrates in powder form described in U.S. Pat. No. 5,609,897 do not comprise Arabic gum.

The problem of providing a suitable emulsion or solution containing Arabic gum also occurs in other technical fields. For example, the production of paints or inks containing certain pigments, such as pigment black 7 or the like, requires the use of a matrix agent such as Arabic gum for mediating an emulsion of the pigments. However, also in this context, the above mentioned problems concerning the dissolution kinetics of Arabic gum exist.

Therefore, it is an object of the present invention to provide an Arabic gum material exhibiting increased dissolution kinetics, i.e. increased dissolution speed. Thus, it is an object of the invention to provide an easy to handle and readily dissolvable Arabic gum material. Advantageously, said Arabic gum material is particularly suitable for the preparation of beverages. Furthermore, it is an object of the present invention to provide an Arabic gum comprising composition exhibiting improved dissolution kinetics for the components of the composition, such as for organic salts. Furthermore, said Arabic gum material and Arabic gum comprising composition should be producible in an easy and cost saving way.

The object of the invention is solved by the claimed subject-matter.

SUMMARY OF THE INVENTION

The present invention provides a wet granulation process comprising contacting a material to be granulated, preferably a powder material, with a granulating liquid, wherein the granulating liquid comprises Arabic gum. The concentration of Arabic gum in the granulating liquid is preferably from about 20% to about 30% (w/v), most preferably about 25% (w/v).

The material to be granulated may comprise Arabic gum and/or further compounds or components. Preferably, the material to be granulated comprises Arabic gum, preferably in an amount of at least 20% (w/w), more preferably in an amount of at least 50% (w/w). Preferably, the material to be granulated comprises one or more metal salt(s), preferably one or more organic metal salt(s), wherein preferably the metal ion of the metal salt is a monovalent or bivalent metal ion, such as potassium, selenium, sodium, lithium, calcium, magnesium, zinc, or iron. Preferably, the counter ion of the metal salt is an organic counter ion, such as lactate, gluceptate, glutamate, citrate, malate, pantothenate, acetate, gluconate, ascorbate etc. A preferred ratio of granulating liquid to material to be granulated applied in the process according to the present invention is between about 1:1 and about 1:10 (volume of granulating liquid, e.g. in ml:weight of material to be granulated, e.g. in g), preferably about 1:1 and about 1:6, more preferably between about 1:1 and about 1:4, most preferably between about 1:2 and about 1:4. It is preferred that the granulating liquid is finely dispersed when contacted with the material to be granulated, for example, by spraying or nebulising the granulating liquid. The wet granulation process according to the present invention may be any suitable wet granulation process preferably selected from the group consisting of fluidized bed granulation, mixing granulation, extruder granulation, disc granulation, and roller granulation, wherein fluidized bed granulation is particularly preferred. Preferably, the granulate material obtained by the process according to the present invention comprises at least 5% (w/w), such as 8% (w/w), preferably at least 50% (w/w) Arabic gum.

In one embodiment, the process according to the present invention is for increasing dissolution kinetics of the material to be granulated, wherein "increasing dissolution kinetics" means "increasing dissolution speed". For example, the method according to the present invention is preferably for increasing dissolution kinetics of Arabic gum in an aqueous solvent and/or for increasing dissolution kinetics and/or solubility of a metal salt, preferably of an organic metal salt as described herein. In one embodiment, the method according to the present invention is for improving bioavailability of a metal salt, preferably of an organic metal salt as described herein.

In a preferred embodiment, the material to be granulated is mixed before granulating so as to result in granulate material, wherein the ingredients of said material, in particular Arabic gum, are evenly distributed throughout an individual particle of the granulate material. To this end, a granulation process is advantageously selected that yields granulate material, wherein individual particles are substantially homogenous in structure. Preferably, the granulate material according to the invention does not comprise more than one distinct compartment or layer, such as would be the case, for example, in a bi- or multilayered granulate. Furthermore, the granulate material according to the invention does preferably not comprise a plurality of distinct compartments, such as a core structure and one or more coating or adhesive layer(s), respectively. In particular, the granulate material according to the invention does preferably not comprise an adhesive layer comprising Arabic gum. In one embodiment, the granulate material according to the invention does not consist of preferably does not contain, microcellulose. In another embodiment, the granulate according to the invention comprises microcellulose but does not have any coating or outer layer comprising a gum arabicum hydrocolloid. Moreover, individual particles of the granulate material according to the invention do preferably not contain pores in the form of internal channels. The granulate material according to the invention does preferably not contain a distinct granulation seed or compartment structure, such as a granulation seed, nucleus or core, which could serve, for instance, as a starting material in a granulation process.

Furthermore, the present invention provides a granulate material comprising Arabic gum, wherein the individual granules making up the granulate material are porous, preferably exhibiting a mean porosity of at least 15%, preferably of at least 20%, more preferably of at least 30%. Preferably, the mean porosity of the individual granules is between about 15% to about 75%, preferably between about 20% to about 70%, wherein the diameter of the pores, which preferably exhibit an essentially round shape, is preferably between about 5 μm and 150 μm, preferably between about 10 μm and 100 μm.

The granulate material according to the present invention comprises Arabic gum preferably in an amount of at least 5% (w/w), such as of at least 8% (w/w), more preferably of at least 15% (w/w), such as of at least 20% (w/w), even more preferably of at least 50% (w/w), such as of at least 60%, 70%, or 80% (w/w). In a preferred embodiment, the granulate material according to the present invention further comprises one or more further compounds, such as one or more metal salt(s), preferably one or more organic metal salt(s) as described herein.

The mean particle size of the granules making up the granulate material according to the present invention is preferably about 200 μm to about 600 μm, preferably about 300 μm to about 400 μm. Preferably, the shape of the granules is irregular, wherein preferably the surface of the granules is rutted. Furthermore, it is preferred that pores within the granules are spatially connected with the surface of the granules, preferably via rills forming the rutted surface.

The granulate material according to the present invention is preferably completely dissolvable in an aqueous or alcoholic aqueous solvent (e.g. at about neutral pH) at room temperature by manual stirring or by stirring using a magnetic stir bar at 100 rpm at a concentration of 5% (w/v) within 5 minutes, preferably within 2 minutes, more preferably within less than 1 minute, for example within about 30 seconds. Such aqueous solvents may be, for example, table or mineral water, fruit juices, or milk.

The granulate material according to the present invention is preferably obtainable by a wet granulation process, preferably by the wet granulation process according to the present invention. Thus, the present invention provides a granulate material obtainable by the wet granulation process according to the present invention.

Furthermore, the present invention provides a composition comprising the granulate material according to the present invention, for example for preparing a liquid, preferably a drinkable liquid.

In a preferred embodiment, the granulate material according to the invention or the composition according to the invention does not comprise astringents (such as tannins), honey solution or tricalcium phosphate.

The present invention also provides the granulate material according to the present invention and the composition according to the present invention for use as a medicament and/or for use as a dietary supplement. For example, the present invention relates to the granulate material according to the present invention and the composition according to the present invention for use in the treatment or prevention of a metal ion deficiency, such as iron, calcium, zinc, potassium, selenium, lithium, sodium, or magnesium deficiency or for use in the treatment or prevention of a disorder amenable to treatment or prevention by metal ion supplementation. Furthermore, the present invention provides the use of the granulate material according to the present invention and the use of a composition according to the present invention as dietary supplement.

A BRIEF DESCRIPTION OF THE FIGURES

FIG. 1 shows an electron micrograph of a granulate material according to the present invention consisting of Arabic gum and calcium lactate (about 86% Arabic gum). The upper panel represents a 200× magnification, scale bar=500 µm. The lower panel represents a 500× magnification, scale bar=200 µm.

Figure 2:
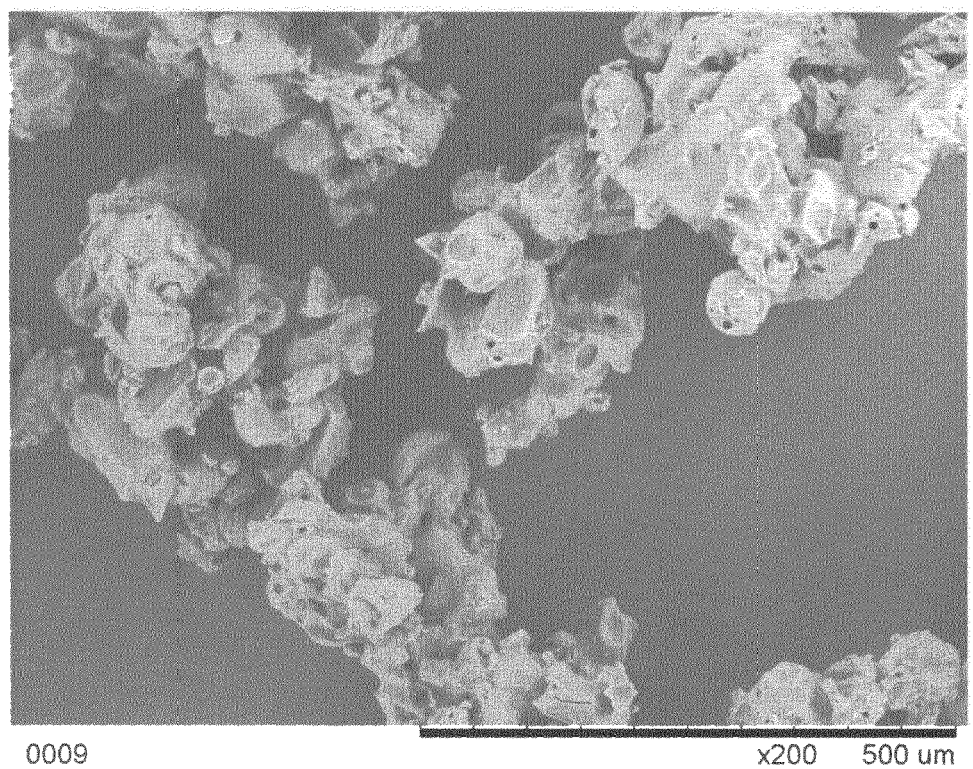
Figure 2:
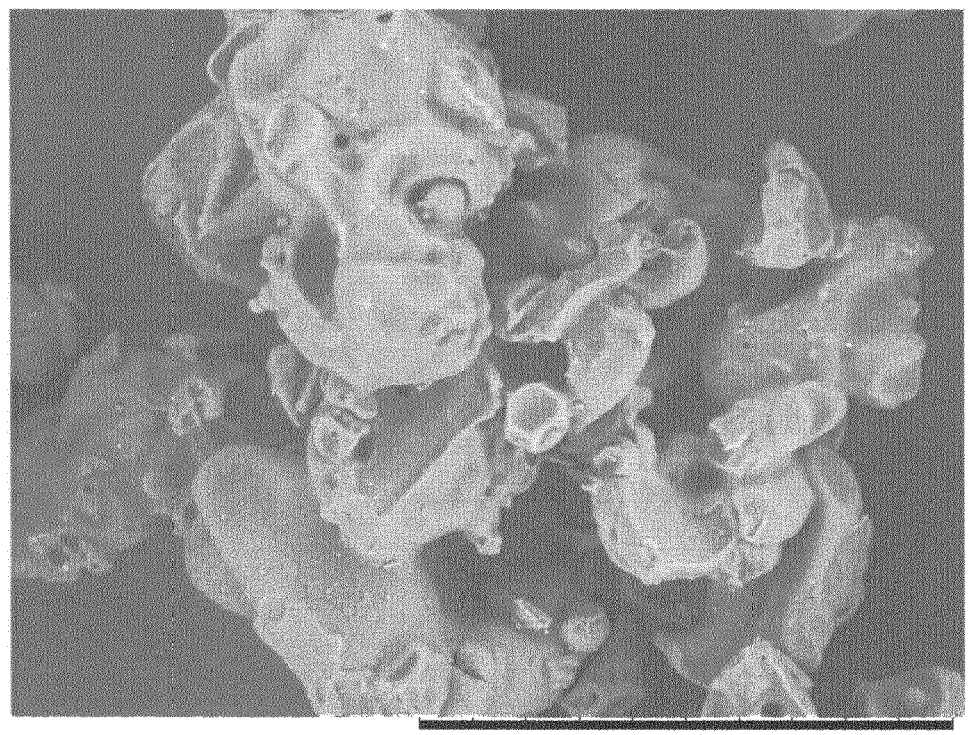

FIG. 2 shows an electron micrograph of a granulate material according to the present invention consisting of Arabic gum and calcium glutamate (about 82% Arabic gum). The upper panel represents a 200× magnification, scale bar=500 µm. The lower panel represents a 500× magnification, scale bar=200 µm.

Figure 3:
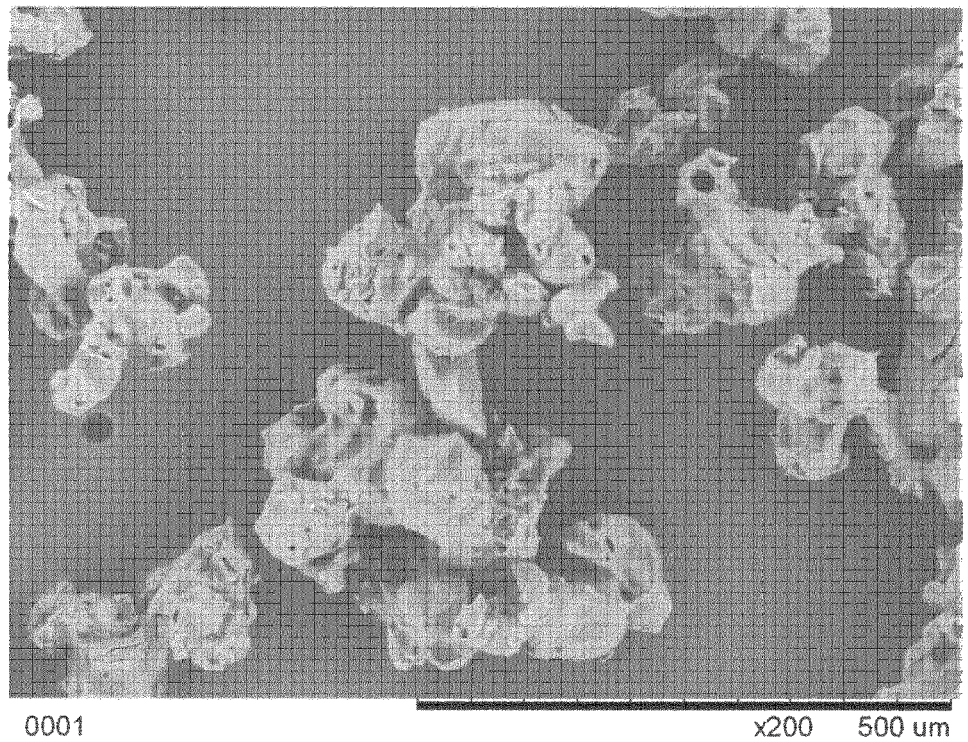
Figure 3:

FIG. 3 shows an electron micrograph of a granulate material according to the present invention consisting of Arabic gum and magnesium lactate (about 84% Arabic gum). The upper panel represents a 200× magnification, scale bar=500 µm. The lower panel represents a 500× magnification, scale bar=200 µm.

Figure 4:
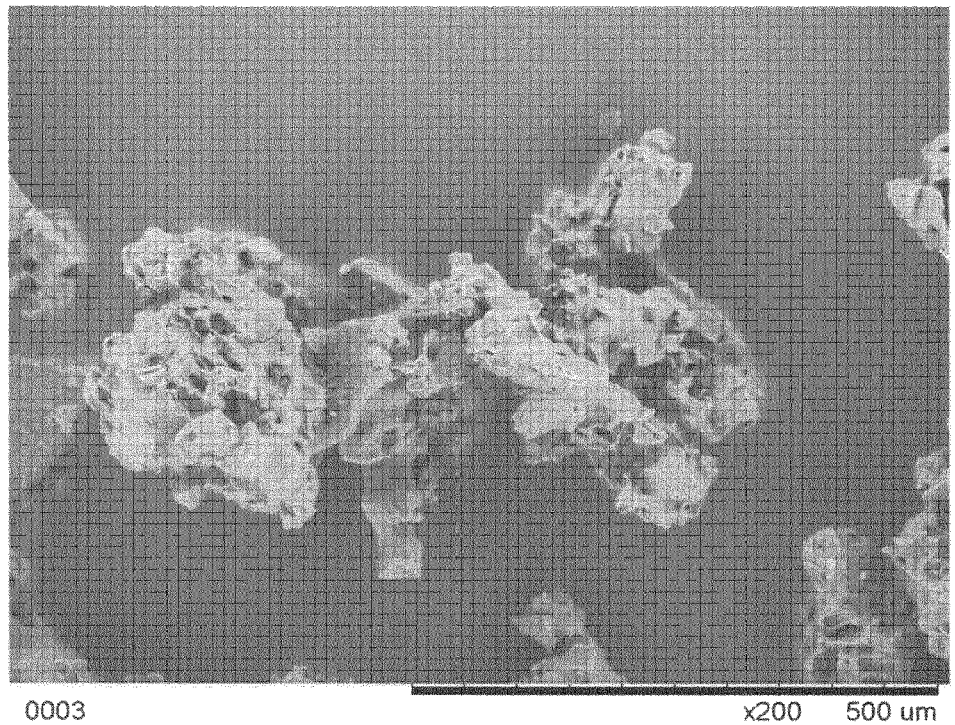
Figure 4:
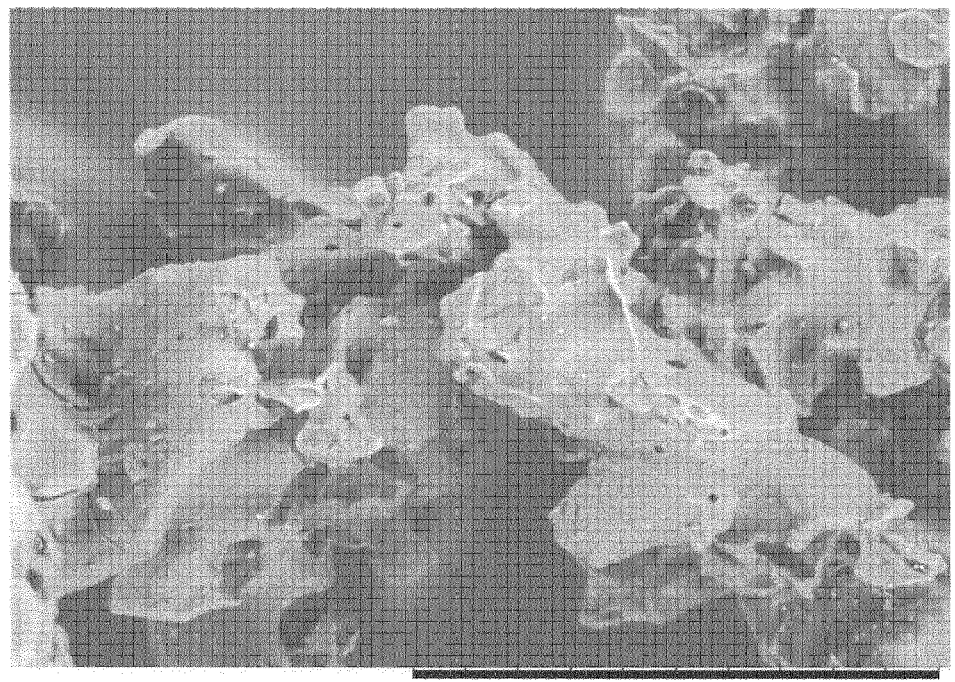

FIG. 4 shows an electron micrograph of a granulate material according to the present invention consisting of Arabic gum and zinc gluconate (about 99% Arabic gum). The upper panel represents a 200× magnification, scale bar=500 µm. The lower panel represents a 500× magnification, scale bar=200 µm.

Figure 5:
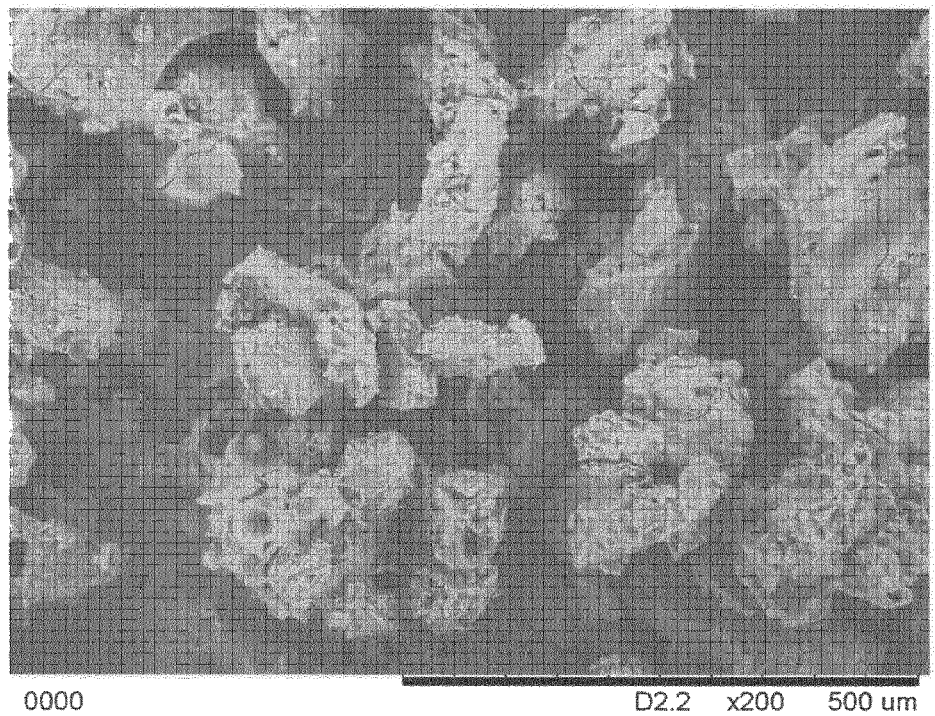
Figure 5:
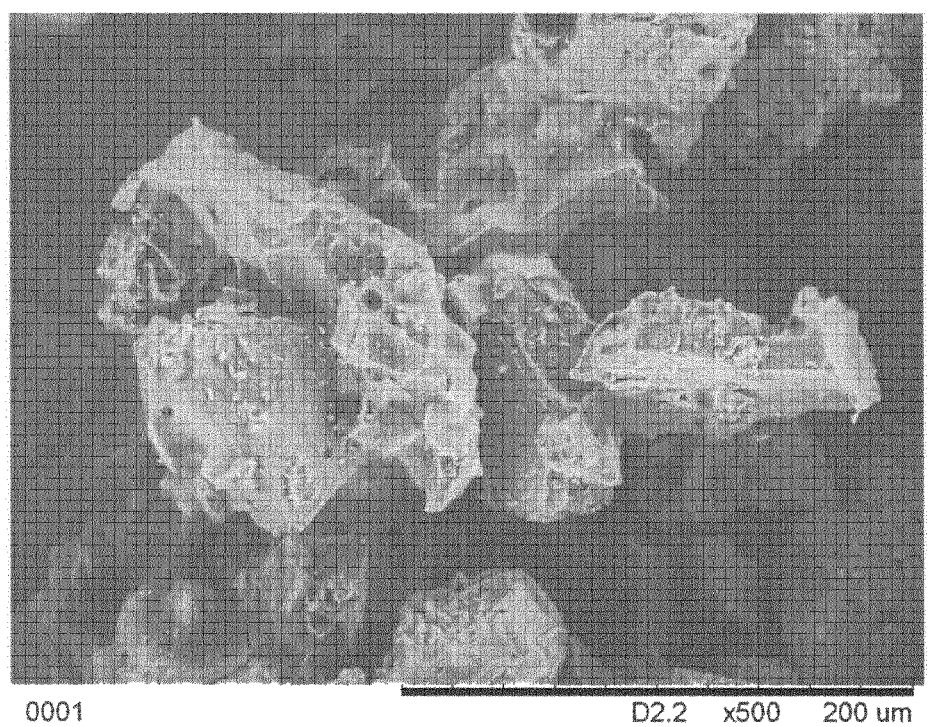

FIG. 5 shows an electron micrograph of a granulate material according to the present invention consisting of Arabic gum, magnesium lactate, calcium gluceptate and zinc gluconate (cf. Example 6a, multi-batch 1/5, about 75% (w/w) Arabic gum). The upper panel represents a 200× magnification, scale bar=500 µm. The lower panel represents a 500× magnification, scale bar=200 µm.

Figure 6:
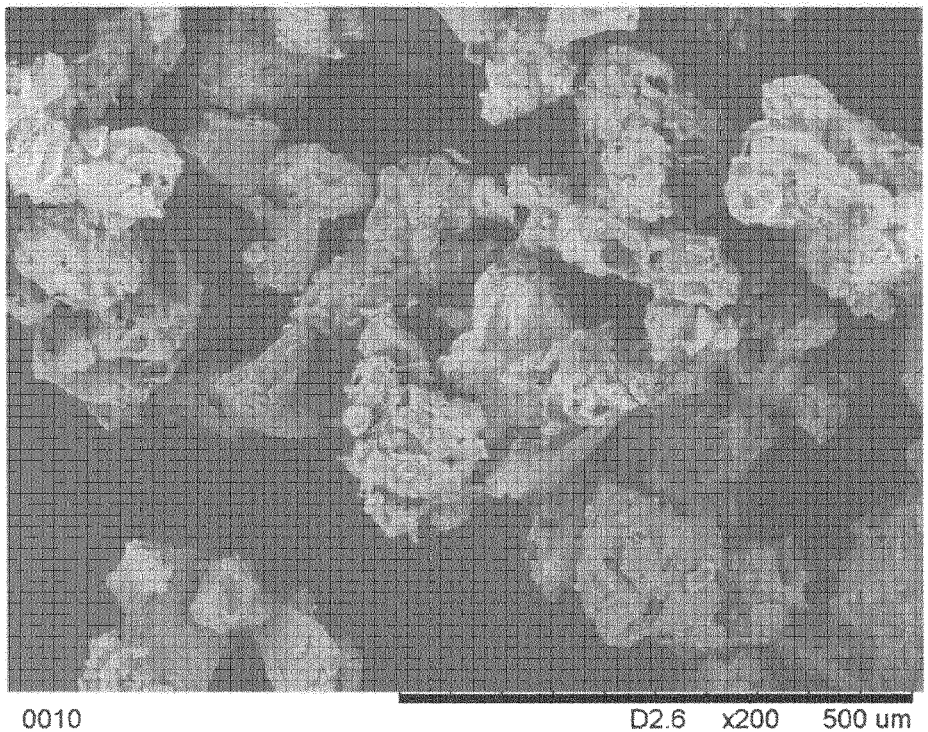
Figure 6:
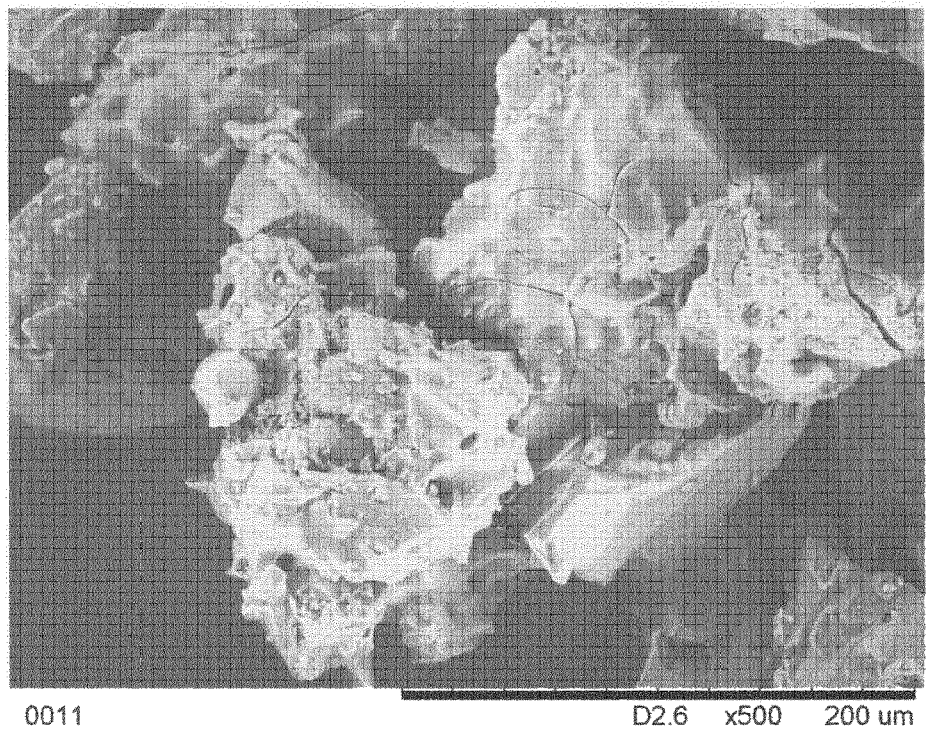

FIG. 6 shows an electron micrograph of a granulate material according to the present invention consisting of Arabic gum, magnesium lactate, calcium gluceptate and zinc gluconate (cf. Example 6b, multi-batch 1/3, about 65% Arabic gum). The upper panel represents a 200× magnification, scale bar=500 µm. The lower panel represents a 500× magnification, scale bar=200 µm.

Figure 7:
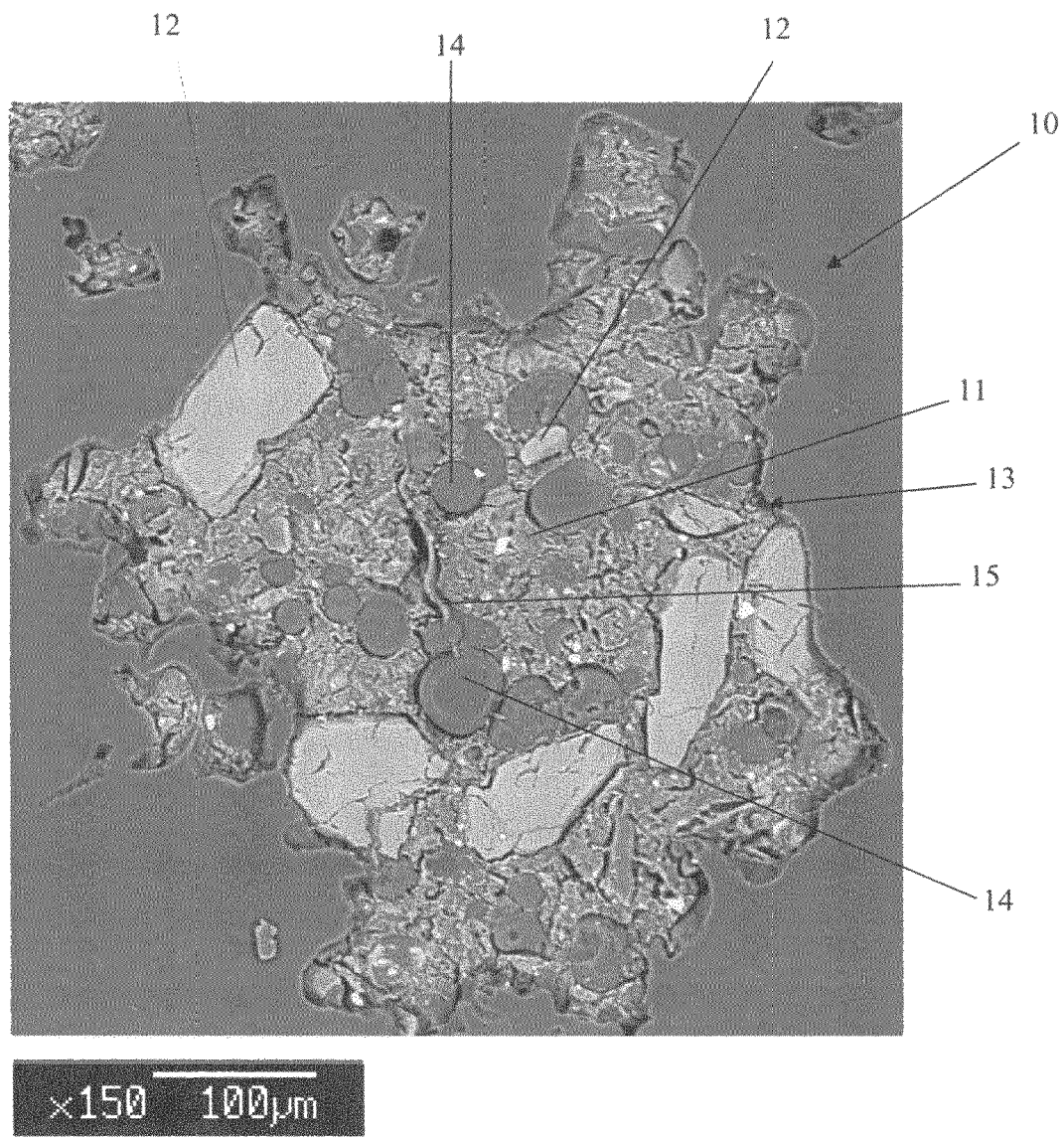

FIG. 7 shows an electron micrograph of a single granule of the granulate material according to the present invention consisting of Arabic gum and magnesium lactate (cf. Example 8 as described below, about 84% Arabic gum). The image is a 150× magnification, scale bar=100 µm.

Figure 8:
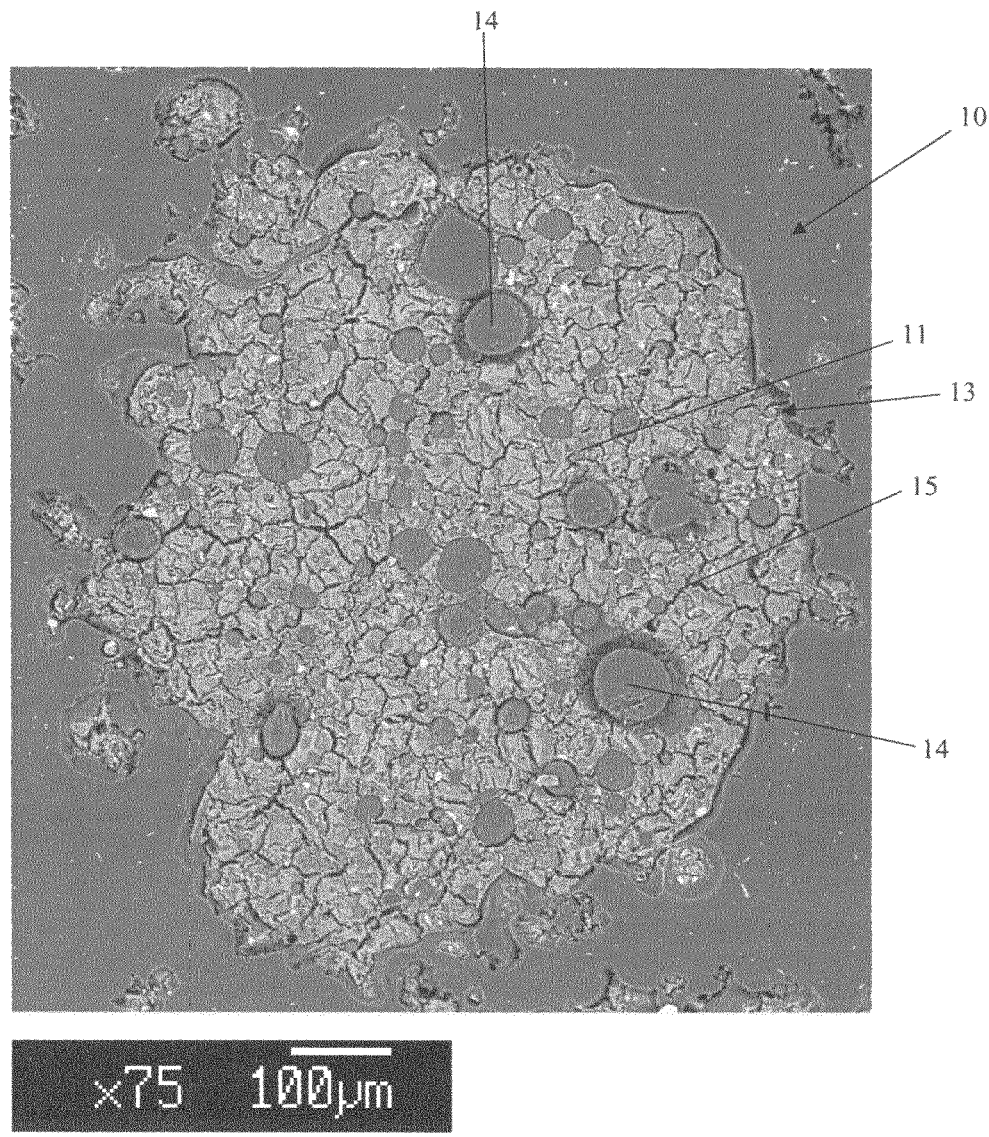

FIG. 8 shows an electron micrograph of a single granule of the granulate material according to the present invention essentially consisting of Arabic gum (cf. Example 1 as described below, 100% Arabic gum). The image represents a 75× magnification, scale bar=100 µm.

Figure 9:
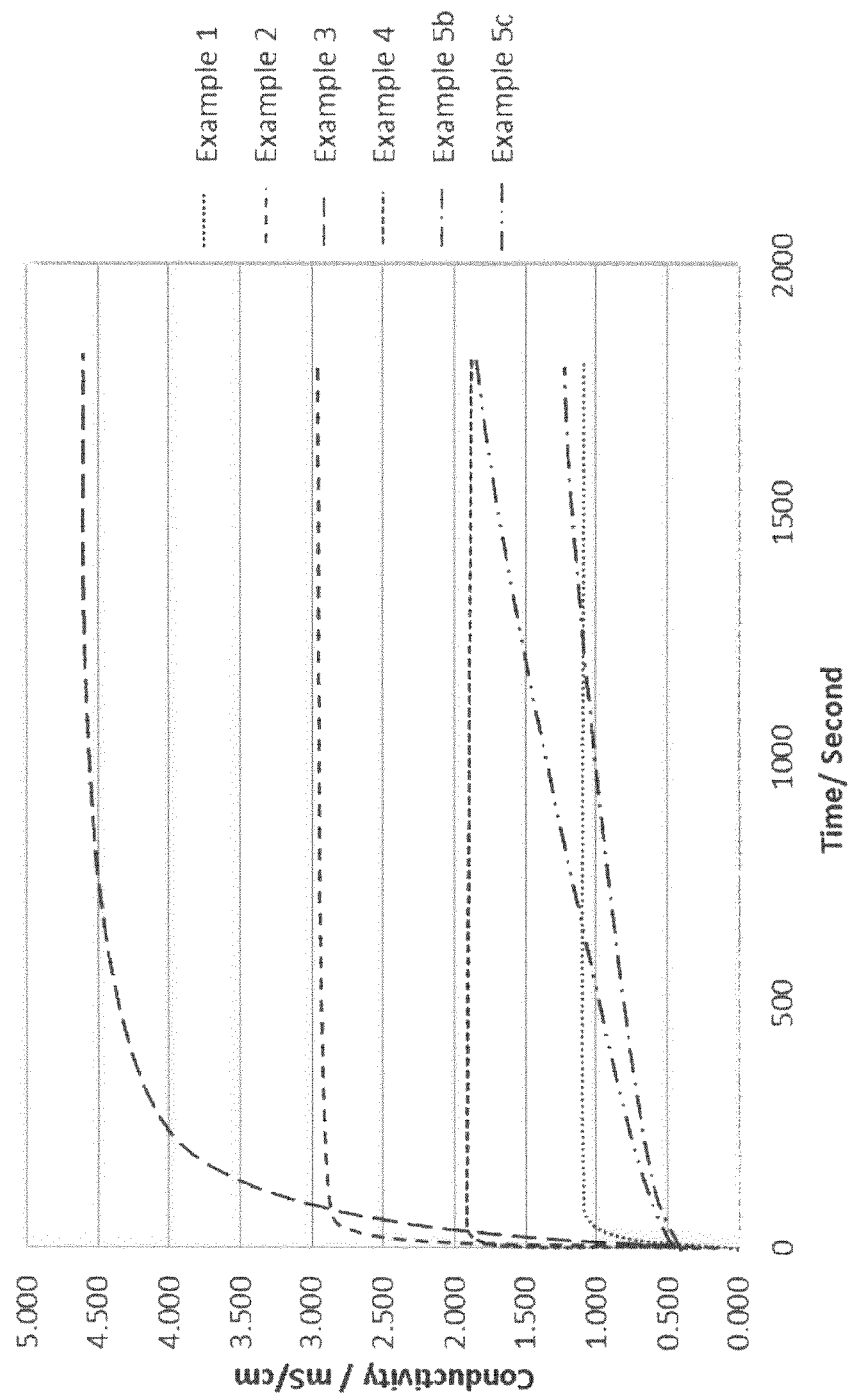

FIG. 9 depicts the results of a dissolution assay providing the dissolution kinetics of the granulate material according to the present invention in comparison to ungranulated material measured by an increase in conductivity (Example 1: granulated Arabic gum; Example 2: granulated Arabic gum calcium gluceptate material, about 79% Arabic gum; Example 3: granulated Arabic gum magnesium lactate material, about 84% Arabic gum; Example 4: granulated calcium gluceptate Arabic gum material, about 8% Arabic gum; Example 5b: powder mix of ungranulated Arabic gum powder and calcium gluceptate, about 79% Arabic gum; Example 5c: powder mix of ungranulated Arabic gum powder and magnesium lactate, about 84% Arabic gum).

FIG. 10 depicts the results of a flow assay using a Copley Scientific automatic flow meter at an orifice size of 1.5 cm determining the flow properties of the samples shown in FIG. 9.

Figure 11:
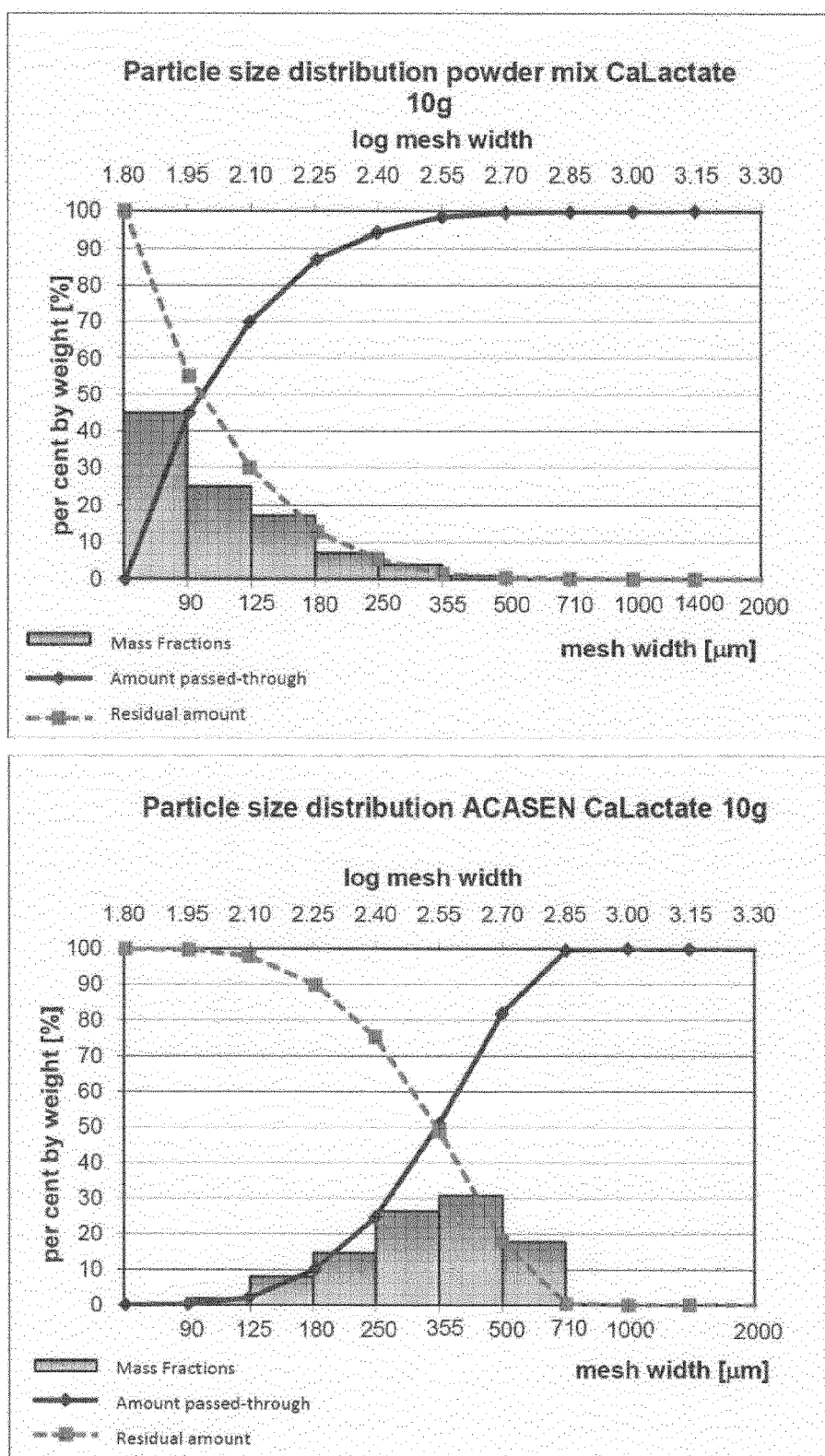

FIG. 11 shows bar diagrams of particle size distributions determined by sieving analysis using the Sieve analyzer "Retsch AS 200 control". The upper panel shows the particle size distribution of the powder mix of Arabic gum and calcium lactate before application to the granulation process according to the present invention. The bottom panel shows the particle size distribution of the granulated material according to the present invention consisting of Arabic gum and calcium lactate; about 86% Arabic gum.

Figure 12:
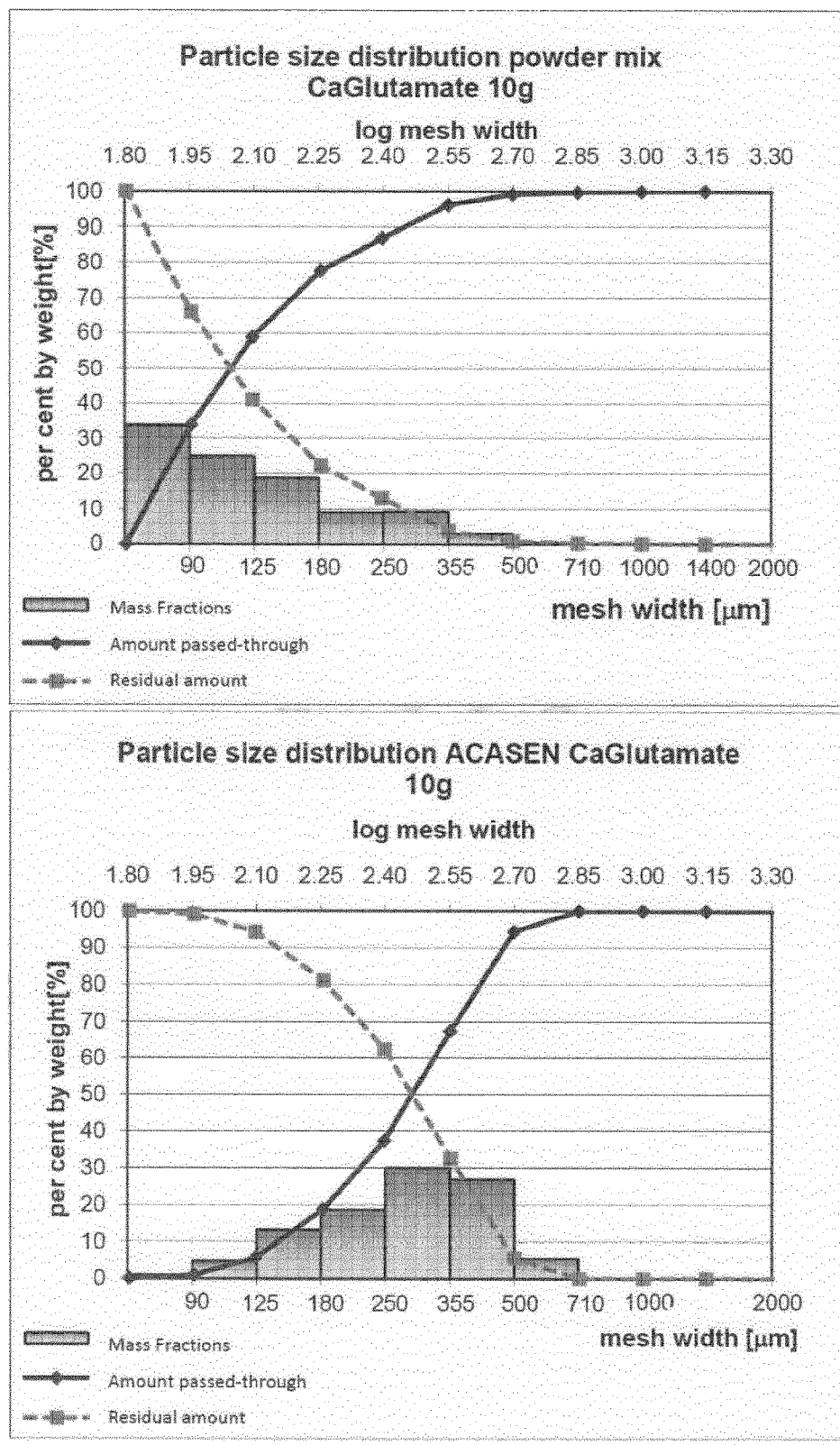

FIG. 12 shows bar diagrams of particle size distributions determined by sieving analysis using the Sieve analyzer "Retsch AS 200 control". The upper panel shows the particle size distribution of the powder mix of Arabic gum and calcium glutamate before application to the granulation process according to the present invention. The bottom panel shows the particle size distribution of the granulated material according to the present invention consisting of Arabic gum and calcium glutamate; about 82% Arabic gum.

Figure 13:
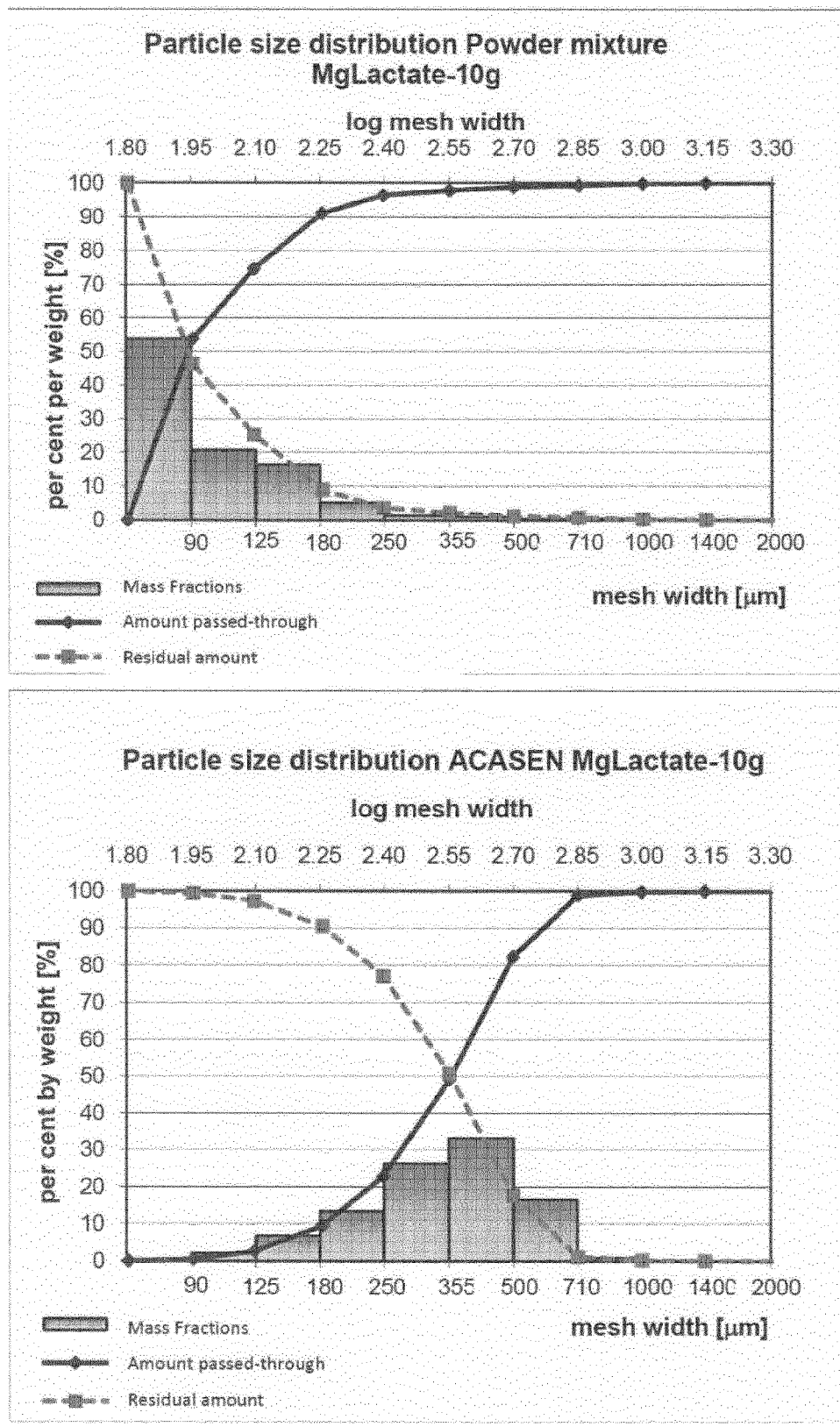

FIG. 13 shows bar diagrams of particle size distributions determined by sieving analysis using the Sieve analyzer "Retsch AS 200 control". The upper panel shows the particle size distribution of the powder mix of Arabic gum and magnesium lactate before application to the granulation process according to the present invention. The bottom panel shows the particle size distribution of the granulated material according to the present invention consisting of Arabic gum and magnesium lactate; about 84% Arabic gum.

Figure 14:
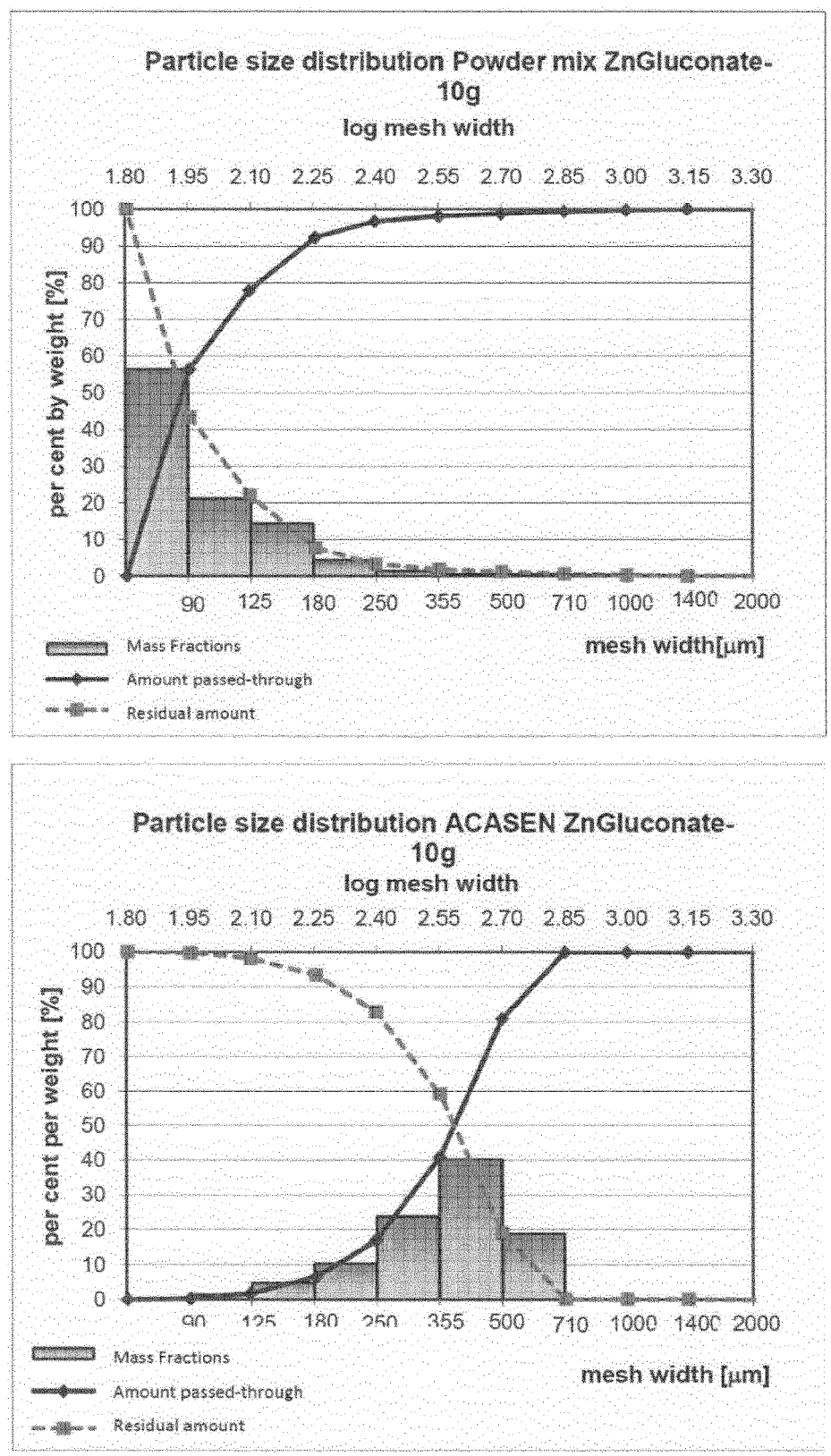

FIG. 14 shows bar diagrams of particle size distributions determined by sieving analysis using the Sieve analyzer "Retsch AS 200 control". The upper panel shows the particle size distribution of the powder mix of Arabic gum and zinc gluconate before application to the granulation process according to the present invention. The bottom panel shows the particle size distribution of the granulated material according to the present invention consisting of Arabic gum and zinc gluconate; about 99% Arabic gum.

Figure 15:
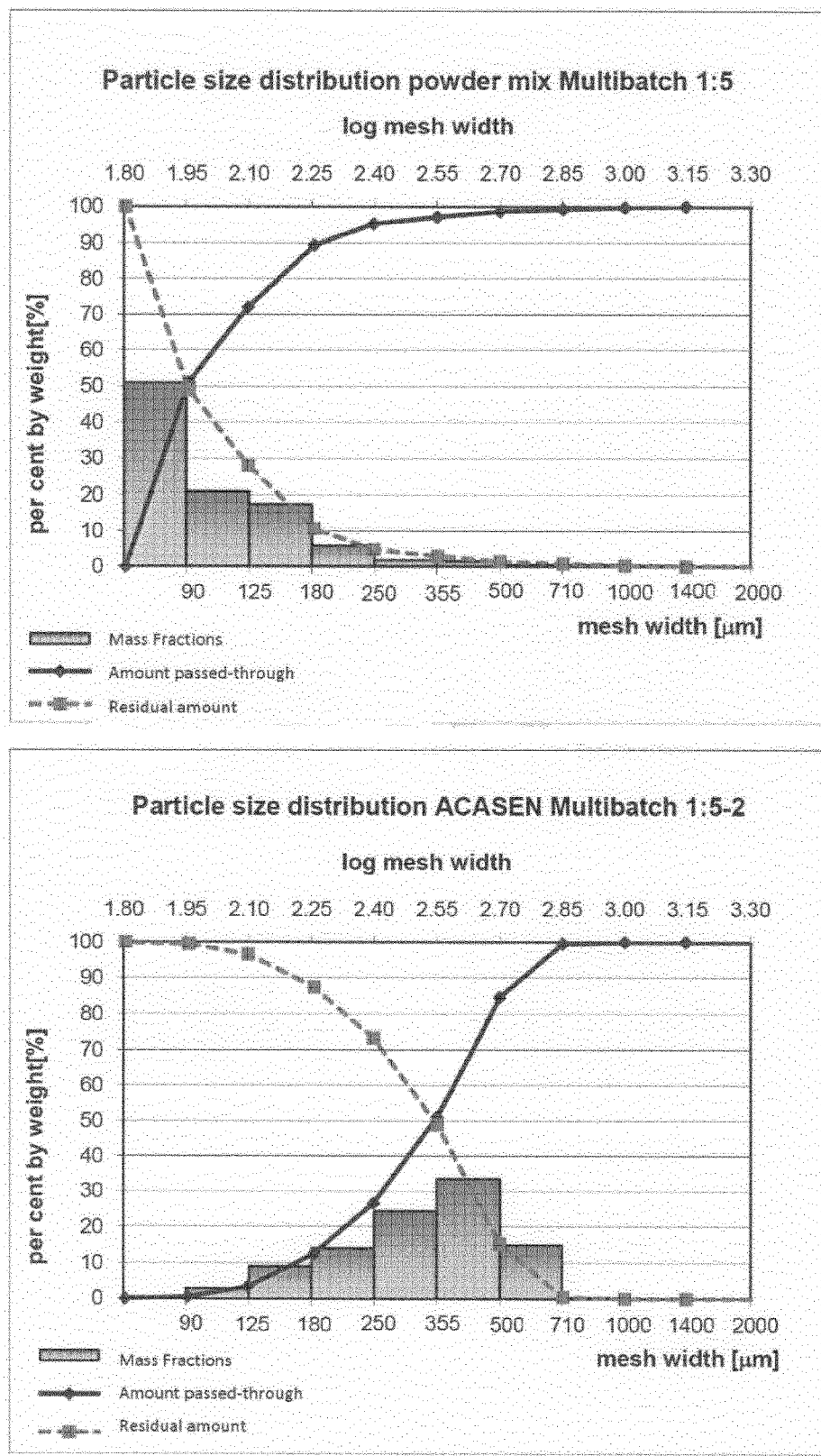

FIG. 15 shows bar diagrams of particle size distributions determined by sieving analysis using the Sieve analyzer "Retsch AS 200 control". The upper panel shows the particle size distribution of the powder mix of Arabic gum, magnesium lactate, calcium gluceptate and zinc gluconate before application to the granulation process according to the present invention. The bottom panel shows the particle size distribution of the granulated material according to the present invention consisting of Arabic gum magnesium lactate, calcium gluceptate and zinc gluconate (Multi-batch 5/1); about 76% Arabic gum.

Figure 16:
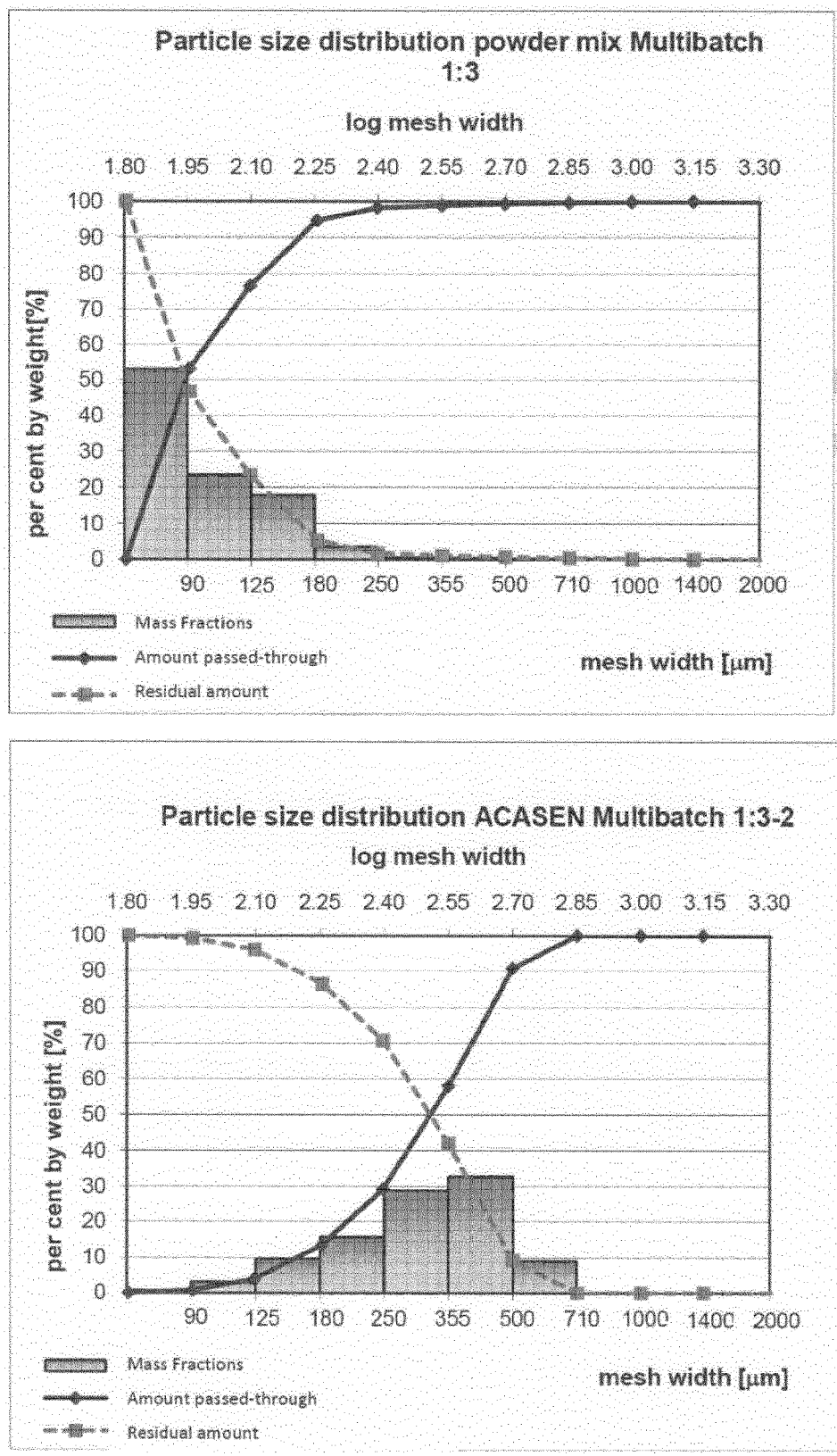

FIG. 16 shows bar diagrams of particle size distributions determined by sieving analysis using the Sieve analyzer "Retsch AS 200 control". The upper panel shows the particle size distribution of the powder mix of Arabic gum, magnesium lactate, calcium gluceptate and zinc gluconate before application to the granulation process according to the present invention. The bottom panel shows the particle size distribution of the granulated material according to the present invention consisting of Arabic gam magnesium lactate, calcium gluceptate and zinc gluconate (Multi-batch 3/1); about 65% Arabic gum.

Figure 17:
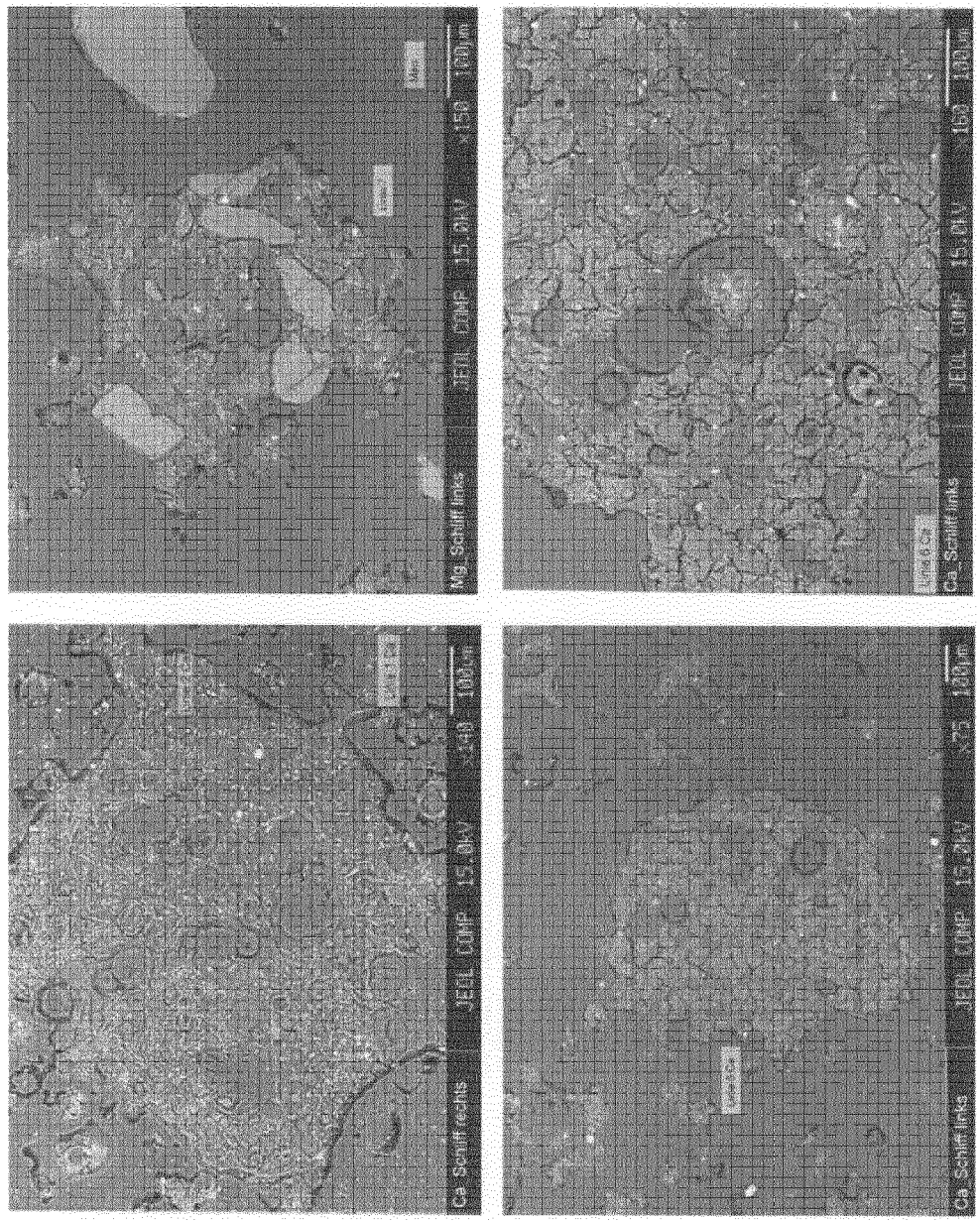

FIG. 17 shows electron micrographs of individual granule sections used for the determination of the porosity of the individual particles. The scale bar represents 100 µm.

DETAILED DESCRIPTION OF THE INVENTION

In a first aspect, the present invention provides a wet granulation process comprising contacting a material to be granulated with a granulating fluid, wherein the granulating fluid comprises Arabic gum. The state of matter of the granulating fluid is preferably liquid at room temperature, e.g. at about 20° C. to about 45° C. Thus, the granulating fluid is preferably a granulating liquid.

The concentration of Arabic gum in the granulating liquid is preferably between about 5% and about 40% (w/v), preferably between about 15% and about 35% (w/v), more preferably between about 20% and about 30% (w/v), even more preferably between about 22% and about 28% (w/v), and most preferably the concentration of Arabic gum in the granulating liquid is about 25% (w/v).

Preferably, the granulating liquid does not comprise honey solution and/or tricalcium phosphate.

The solvent used for dissolving Arabic gum for preparing the granulating liquid may be any solvent suitable for wet granulation and for dissolving Arabic gum at least to a certain extend. For example, a solution of at least 5% (w/v), preferably of at least 10% (w/v), more preferably of at least 15% (w/v), most preferably at least 20% (w/v) should be possible in the solvent used for preparing the granulating liquid. Preferably, the solvent is selected from aqueous and alcoholic aqueous solvents. Preferably, the solvent is water, preferably deionized water, such as distilled water. The solvent is preferably selected based on the intended use of the granulate material. For example, if the granulate material is intended for production of an edible or drinkable product the solvent should be suitable for human ingestion, preferably should be admitted to be used for food production, more preferably should be admitted for production of pharmaceutical compositions. In case the granulate material is intended to be used, e.g. for dye or paint production, the solvent should be, for example, compatible with the ground to be colored etc.

The granulating liquid may further comprise other components or compounds, such as flavoring agents, aromatic substances, sweeteners, sugars, coloring agents, preferably, natural coloring agents, emulsifiers.

Suitable flavouring agents are known in the art and comprise natural as well as synthetic flavours. Various substances of mostly plant origin, such as spices, herbs, roots, essences, and essential oils, can be used as natural flavours. The flavouring agents responsible for a particular flavour are generally esters, aldehydes, ketones, alcohols and ethers, which may also be synthesized chemically. Examples of synthetic flavour additives comprise amyl acetate for banana, methyl anthranilate for grapes, ethyl butyrate for pineapple, etc. A mixture of different substances may as well be used in order to create a certain flavour.

In addition, the term "flavouring agents" as used in the context of the present invention may also relate to flavour enhancers, such as monosodium glutamate (MSG) or yeast extract, as well as to taste-masking agents.

Substances that can be used as sweeteners comprise sugars, such as sucrose, fructose, glucose, dextrose or maltose, as well as substances having a sweet taste, which are commonly used to substitute for sugar. Polyols or sugar alcohols, such as sorbitol, mannitol, xylitol or isomaltate, are frequently used as sweeteners. Sweet substances of plant origin as well as synthetic compounds are known that have low or no nutritional value. Examples of such substances comprise glycyrrhizhin, steviosides, thaumatin, aspartame, acesulfame K, sucralose or neotame.

Suitable coloring agents may be of synthetic or natural origin, wherein natural food colors, such as annatto, betanin, caramel, carmine, carotene, carthamanin, curcumin or turmeric, are preferred.

Emulsifying agents, e.g. lecithin, agar, alginates, emulsifying wax, carrageenan, glycerol, monoglycerides, diglycerides, monostearate, cetostearyl alcohol, glycerides, pectin, may further be added.

For example, such components or compounds, e.g. an aromatic substance, such as a flavoring agent, may be present in the granulating liquid at a concentration of about 0.1% to about 1% (w/w), more preferably at a concentration of about 0.1% to 0.5% (w/w) in relation to the weight of the end product (i.e., the granulate material resulting from the process of the present invention, preferably the dried granulate material).

Preferably, the granulating liquid is prepared by mixing Arabic gum and optionally other ingredients with the selected solvent, e.g. distilled water, deionized water or the like. Preferably, Arabic gum is added stepwise to the solvent, while the solvent is optionally stirred carefully. The stirring is preferably performed such that the formation of air bubbles in the solution is prevented. It is preferred that the Arabic gum is in the form of a powder before adding it to the solvent. Accordingly, Arabic gum raw material may be processed into powder form before dissolution in the solvent, e.g. using known methods for preparing powders, e.g. milling, grinding, chaffing or the like or spray drying etc.

In a preferred embodiment, an Arabic gum raw material is used, wherein individual particles have a mean grain size of 1 to 100 µm as determined, for example, by sieving analysis, preferably of 1 to 20 µm, more preferably of 1 to 10 µm, wherein the distribution of the particle sizes is preferably such that at least 80%, more preferably at least 90%, even more preferably at least 95% of the particles have a size, which is characterized in that it varies not more than 30%, preferably not more than 25%, even more preferably not more than 20% from said mean values.

In another embodiment, an Arabic gum raw material is used, wherein the individual particles have a mean grain size of 100 to 250 µm as determined, for example, by sieving analysis, preferably of 100 to 150 µm, more preferably of 100 to 130 µm, wherein the distribution of the particle sizes is preferably such that at least 80%, more preferably at least 90%, even more preferably at least 95% of the particles have a size, which is characterized in that it varies not more than 30%, preferably not more than 25%, even more preferably not more than 20% from said mean values.

Alternatively, an Arabic gum raw material may also be used, wherein the individual particles have a mean grain size of 50 to 150 µm as determined, for example, by sieving analysis, preferably of 60 to 140 µm, more preferably of 70 to 120 µm, wherein the distribution of the particle sizes is preferably such that at least 80%, more preferably at least 90%, even more preferably at least 95% of the particles have a size, which is characterized in that it varies not more than 30%, preferably not more than 25%, even more preferably not more than 20% from said mean values.

Preferably, a desired particle size of an Arabic gum raw material is obtained by techniques known in the art, e.g., milling, grinding and/or chaffing.

In addition, the Arabic gum raw material may undergo one or more mechanical and/or chemical cleaning steps before entering the granulation process. In one embodiment, the Arabic gum raw material is mechanically pre-cleaned. The Arabic gum raw material may optionally also be sterilized, wherein a temperature of preferably at least 65° C. is employed. Additional grinding steps are preferably used for mechanical cleaning of the raw material. By-products and contaminants are preferably separated from the Arabic gum raw material to be processed by air separation ("winnowing"). In a preferred embodiment, said cleaning steps may be employed in combination. In a further preferred embodiment, the individual steps are carried out sequentially, wherein a mechanical pre-cleaning step is followed by a sterilization step, a grinding step and an air separation step. The sterilization step may take place before or after grinding.

Preferably, the amount of granulating liquid used in the wet granulation process according to the present invention is less than about 57% (w/w), preferably less than about 50% (w/w), preferably between about 10% to about 50% (w/w), more preferably between about 15% to about 50% (w/w) of the total mass of material entering the wet granulation process (i.e. granulating liquid+material to be granulated (powder mix)). In a particularly preferred embodiment, the amount of granulating liquid used in the wet granulation process is between about 17% and about 25% (w/w). For example, if the total mass of the material entering the wet granulation process is 1000 g, the mass of the granulation fluid is preferably less than about 570 g, more preferably less than about 500 g, preferably between about 100 g and about 500 g, even more preferably between about 150 g and about 300 g. Preferably, the density of the granulating liquid is between about 0.5 and about 2.5 g/ml, preferably between about 1.0 and 2.0 g/ml, more preferably between about 1.2 and 1.5 g/ml, such as about 1.3 g/ml. However, the density of the granulating liquid may vary depending on the further compounds or components comprised by the granulating liquid.

Preferably, the ratio of granulating liquid (e.g. sprayable liquid) to material to be granulated (e.g. powder) is between about 1:1 and about 1:10 (volume of granulating liquid, e.g. in ml:weight of material to be granulated, e.g. in g), preferably about 1:1 and about 1:6, more preferably between about 1:1 and about 1:5, even more preferably between about 1:2 and about 1:5, most preferably the ratio of granulating liquid to material to be granulated is between about 1:2.5 and about 1:5. Thus, for example, 100 ml of a 25% (w/v) solution of Arabic gum, preferably in distilled water, may be used for granulating 250 g material, preferably powdered material, which represents a 1:2.5 ratio as set forth above.

Variations in the amount of granulating liquid used for treatment of the material to be granulated may influence dispersing time of the granulating liquid, e.g. the spraying time, which might affect structure of the formed granulate, occurrence or non-occurrence of clumping and solubility of the obtained granulate material. For example, while all of the cited ratios yield a product exhibiting enhanced dissolution kinetics and other advantageous properties, such as less clumping and good flow ability, short spraying and drying time and particularly good solubility and dissolution kinetics are achieved at a ratio of granulating liquid to material to be granulated. e.g. powder, between about 1:3 (ml/g) and about 1:5 (ml/g).

In a preferred embodiment of the method according to the present invention, the granulating liquid is dispersed, preferably finely dispersed, before or when contacted with the material to be granulated. The term "finely dispersed" means that the granulating liquid is broken up into drops, preferably into small drops, such as a spray. In other words, it is preferred that the granulating liquid is not contacted with the material to be granulated as a continuous liquid, but in drop form, for example, as spray. The granulating liquid may be dispersed by any known dispersing technique, for example, by spraying, nebulising, sprinkling, drizzling, dripping, dropping, sparkling, or sputtering the granulating liquid. Suitable instruments for dispersing the granulating liquid are, e.g. nozzles or nebulizers. It is particularly preferred that the granulating liquid is sprayed onto or within the material to be granulated.

Preferably, the granulating liquid is contacted with the material to be granulated over a period of time. Thus, it is preferred that the distribution of the amount of dispersed granulating liquid used for the granulation process extends over a certain period of time, go such as over 5 minutes to a few hours. Preferably, the dispersing time, i.e. the duration of dispersing the granulating liquid used for the wet granulation process, e.g. by spraying, is about 15 minutes to about 2 hours, preferably about so minutes to about 1 hour, such as between about 30 and 45 minutes. Thus, the time for dispersing the entire granulating liquid on to the material to be granulated is preferably at least about 15 minutes, more preferably at least about 20 minutes. Preferably, the time for dispersing the entire granulating liquid on to the material to be granulated is preferably less than 50 minutes.

The dispersing rate, such as the spraying rate, of the granulating liquid may vary throughout the granulation process. For example, in the beginning of the granulation process the dispersing rate, e.g. the spraying rate, may be low and is increased during the granulation process. For example, if a GLATT GPCG2 Labsystem fluidized bed granulator is used for the wet granulation process according to the present invention, the spray rate may be adjusted to a setting between 8 and 12 of the apparatus. Preferably, the spray rate is adjusted to the setting 8 for a few minutes, such as for 5 to 15 minutes, then the spray rate may be increased to setting 10 for a few minutes, and then optionally the spray rate may be adjusted to setting 12 of the apparatus until the granulating liquid has been fully dispersed. Preferred dispersing rates, such as spraying rates, are between 1 ml/min and 20 ml/min, preferably between 2 ml/min and 15 ml/min, more preferably between 3 ml/min and 10 ml/min.

Any wet granulation process known to the skilled artisan may be used in the context of the present invention, such as fluidized bed granulation, mixing granulation, extruder granulation, disc granulation, or roller granulation. Preferably, the wet granulation process according to the present invention is a fluidized bed granulation process. Thus, in a preferred embodiment, the material to be granulated, preferably in powdered form, is fluidized in a fluid bed by a fluid flow, such as by an air flow, while being contacted with the, preferably dispersed, granulating liquid, for example, while being sprinkled or sprayed etc. with the granulating liquid.

Independently from the granulation process applied in the specific case, the material to be granulated is preferably mixed before granulating so as to result in granulate material, wherein the ingredients of said material, in particular Arabic gum, are evenly distributed throughout the individual particles of the granulate material. To this end, a granulation process may be selected that yields granulate material, wherein individual particles are substantially homogenous in structure and composition. Accordingly, processes involving granulation seeds, cores or nuclear structures or processes leading to layers and coatings in the granulate material are preferably not employed according to the invention.

A fluid-bed set up, e.g. in a fluidized bed granulator, typically comprises a heatable tower which comprises the material to be granulated, e.g. a powder mix. The material to be granulated is positioned within a flow passage and a fluid, such as air, which may be heated, is flowing through the material to be granulated to produce a fluidized bed. The skilled person is well aware which fluid flow is suitable for generating an appropriate fluidized bed for fluidized bed granulation. The appropriate fluid flow as well as the temperature of the fluid (e.g. the air) will depend on the properties of the material to be granulated and might vary throughout the granulating process. Furthermore, such apparatus typically comprises means for dispersing the granulating liquid, e.g. for spraying the granulating liquid on to the material to be granulated. e.g. a powder or powder mix, for example, one or more nozzles or nebulizers. The temperature of the fluid used for generating the fluidized bed, such as air, may be adjusted, for example, by using heating elements. A moderately increased temperature of the fluid such as the air is beneficial, since it accelerates the drying process.

Preferably, the wet granulation process according to the present invention, such as the fluidized bed granulation process, is performed at ambient temperatures, such as at a temperature of between about 20° C. and about 50° C., preferably between about 25° C. and about 40° C., more preferably between about 30° C. and about 40° C. Preferably, the temperature of the product during the granulation process is not above 60° C., more preferably not above 55° C. In a most preferred embodiment, the product temperature within the granulating apparatus, such as a fluidized bed granulator, during the granulation process is kept at about 30° C. to about 35° C. In a fluidized bed granulator, the product temperature may be adjusted, for example, by adjusting the temperature of the air flow used for generating a fluidized bed of the material to be granulated.

In a preferred embodiment, the material to be granulated, e.g. the powder or powder mix, is pre-warmed before it is contacted with the granulating liquid. For example, pre-warming of the material to be granulated, e.g. the powder, may be performed by:

pre-warming the tower of a fluidized bed granulator, preferably to a temperature between about 20° C. and about 50° C., more preferably to a temperature between about 25° C. and about −45° C., even more preferably to a temperature between about 30° C. and about 40° C., for example to about 40° C., filling the powder into the pre-warmed tower, and operating the fluidized bed granulator without dispersing the granulating liquid, e.g. generating a fluidized bed with warmed fluid, such as air, for e.g. a few minutes, such as about 5 minutes, before beginning to disperse the granulating liquid.

Spraying the liquid over the pre-warmed solid fraction leads to a first granulation layer. The particle size of the granules may be regulated by modification of the spray rate and/or by regulation of the tower's volume flow. Thus, bigger granules may be produced by increasing the spray rate.

After dispersion of the granulating liquid, e.g. by spraying, is completed, the granulate material may flow and dry inside the fluid bed for a few minutes, e.g. five to ten minutes, in order to decrease the product moisture content. The moisture content affects the particle size of the end product. Another possibility for adjusting the particle size of the end product is regulating the time for drying. Thus, a long time period for drying will decrease the particle size of the end product. A further drying step may be performed by using a drying cabinet. This is particularly advantageous if small particle sizes are desired or if the desired moisture content cannot be achieved within an appropriate time within the fluidized bed. Accordingly, in a further embodiment, the inventive process further comprises a step of drying the obtained granulate material after contacting of the material to be granulated with the granulating liquid, e.g. by spraying in a fluidized bed granulator, is completed. Thus, drying the granulate material may be performed inside the fluidized bed granulator and/or in a drying cabinet. It is also possible to dry the granulate material in a first drying step inside the granulator, such as the fluidized bed granulator, and then, in a subsequent second drying step, in a drying cabinet.

Irrespective of the used wet granulation process, the granulate material obtained by the process may be dried. For example, the granulate material may be dried with or without fluid flow, e.g. with or without air flow, for about 1 to about 20 minutes, preferably for about 2 to about 15 minutes, more preferably for about 4 to about 15 minutes, even more preferably for about 5 to about 10 minutes at preferably ambient temperatures, as specified above, of preferably not more than 60° C., more preferably not more than 55° C. Other time periods and temperatures for drying are possible. They have to be adapted to the desired size of the granules of the granulate material and the desired degree of residual moisture.

A preferred degree of residual moisture of the granulate material obtained by the process according to the present invention ranges between 1% and 20% (w/w), preferably between 2% and 15% (w/w), even more preferably between about 5% and about 12% (w/w). The residual moisture content may, for example, be determined using a Mettler Toledo HB43 Halogen apparatus.

The material to be granulated is not particularly limited as long as it is amenable to be granulated by a wet granulation process. Preferably, the material to be granulated is a powder, e.g. a dry solid composed of small particles, a material in crystalline form, preferably fine grained form, or a mixture of a powder and material in crystalline, preferably fine grained form. It is preferred that salts, such as metal salts, optionally used in the material to be granulated are used in fine grained from, such as in powdered crystalline form.

Powders may be produced by any known method for reducing the size of particles, e.g. by mincing, grinding, chopping, crushing, shredding, etc. or by any known method for producing powders such as spray drying. Powdered forms of Arabic gum are commercially available, for example, spray dried Arabic gum or dispersion desiccatum Arabic gum Ph.Eu. (e.g. Sigma-Aldrich, CAS-number 9000-01-5). Arabic gum used in the present invention, e.g. used for the preparation of material to be granulated or as material to be granulated, is preferably a spray dried Arabic gum, a dispersion desiccatum Arabic gum Ph.Eu. or an equivalent material having comparable particle size and particle size distributions and/or structural characteristics. Thus, preferably the material to be granulated comprises or consists of spray dried Arabic gum or a dispersion desiccatum Arabic gum Ph.Eu.

As explained above, Arabic gum raw material is preferably used that has a defined mean grain size, which can be obtained by techniques known in the art, such as milling, grinding or chaffing.

The material to be granulated may be a single compound or may be a mixture of compounds, such as a composition. For example, the material to be granulated may be Arabic gum, such as an Arabic gum powder as described above, any other compound amenable to granulation, or a composition or mixture comprising Arabic gum and one or more other substances, such as metal salts, micronutrients (e.g Q10, carnitine etc.), and/or vitamins etc. Thus, for example, the material to be granulated may be a mixture of an Arabic gum powder and one or more substances, e.g. in powder or fine grained crystalline form. Such mixture of Arabic gum powder and one or more substances, e.g. in powder or fine grained crystalline form are termed herein "powder mixture" or "powder mix". A powder mix may be prepared by mixing the components of the material to be granulated, for example, using a turbular mixer, preferably without using blades or choppers. A preferred material to be granulated, e.g. a preferred powder mix according to the present invention comprises or consists of Arabic gum in powder form as described above and one or more metal salt(s), preferably one or more organic metal salt(s) in powder or fine grained crystalline form.

The mean particle size of the material to be granulated, e.g. of the powdered Arabic gum or a powder mix, entering the wet granulation process is preferably between about 1 μm and about 250 μm, more preferably between about 20 μm and about 150 μm measured by sieving analysis (e.g. using a "Retsch AS 200 control" apparatus), wherein preferably at least 50% (by weight), more preferably at least 60% (by weight) of the particles have a particle size of below 125 μm, and preferably at least 90%, more preferably at least 95% of the particles have a particle size of below 250 μm measured by sieving analysis. That means that preferably at least 95% by weight of the material to be granulated can be found in the sieving experiment below a sieve bottom having a mesh size of 250 μm.

In one embodiment, the material to be granulated comprises, preferably essentially consists of; preferably consists of Arabic gum. In another embodiment, the material to be granulated comprises or consists of one or more compound(s), preferably, one or more compounds that are suitable to be formulated with Arabic gum. Preferably, the material to be granulated comprises one or more compounds which obtain advantageous properties, such as increased solubility or dissolution kinetics, when formulated with Arabic gum. For example, such compounds may be any compounds commonly used in combination with Arabic gum in any field. Thus, such compounds may be used in the food industry, in the pharmaceutical industry, in the cosmetic industry, in the ceramic industry, in the match industry, in the dye, ink, or paint industry, in the adhesive industry etc. For example, the material to be granulated may comprise ink, for example powdered ink or pigments for producing ink.

In a preferred embodiment, the material to be granulated may comprise one or more metal salt(s), preferably one or more organic metal salt(s). Preferably, the metal is a monovalent or bivalent metal, for example, selected from the group consisting of potassium, sodium, lithium, calcium, magnesium, zinc, selenium, and iron. The counter ion of the metal salt is preferably an organic counter ion, for example, selected from the group consisting of acetate, alginate, ascorbate, aspartate, amygdalate, benzoate, borogluconate, carbasalate, carbonate, citrate, cyclamate, dinatriumtetralactate, dobesilate, ferro-phospholactate, folinate, formate, fumarate, glubionate, glucoheptonate, gluconate, glutamate, glycerophosphate, iopodate, ketoglutarate, lactate, lactogluconate, laevulinate, malate, methionate, orotate, oxalate, pangamate, pantothenate, phospholactate, phatalate, picrate, pidolate, propionate, resinate, saccharate (=glucarate), saccharin, sorbate, succinate, etc. For example, the organic counter ion is selected from the group consisting of lactate, gluceptate, glutamate, citrate, malate, pantothenate, acetate, gluconate and ascorbate. Preferred metal ion salts are lactate, such as magnesium lactate or calcium lactate, gluconate, such as calcium gluconate or zinc gluconate, gluceptate, such as calcium gluceptate, and glutamate, such as calcium glutamate. A particular preferred combination—if more than one metal salt is used—is the combination of a magnesium, a calcium and a zinc salt, such as a combination of magnesium lactate, calcium gluceptate and zinc gluconate.

The material to be granulated, e.g. the powder mix, may or may not contain Arabic gum. Both embodiments are possible. Accordingly, in one embodiment, Arabic gum is only present in the granulating liquid, in another embodiment, Arabic gum is present in the granulating liquid as well as in the material to be granulated.

In the embodiment where both components, i.e. the granulating liquid and the material to be granulated, comprise Arabic gum, the material to be granulated preferably comprises between about 65% to about 97.5% (w/w) of the total amount of the Arabic gum used for the granulation process. Thus, preferably, about 2.5% to about 85%, more preferably about 5% to about 15%, such as about 10% of the total amount of Arabic gum used for the wet granulation process according to the invention are used dissolved in the granulating liquid. The remainder is used in the material to be granulated, e.g. the powder or powder mix.

Preferably, the material to be granulated comprises at least 5% (w/w), more preferably at least 15% (w/w), more preferably at least 20% (w/w), more preferably at least 40% (w/w), even more preferably at least 50% (w/w), even more preferably, at least 60% (w/w), for example, about 64%, about 70%, about 75% etc. Arabic gum, preferably Arabic gum powder. In one embodiment, the material to be granulated consists of Arabic gum. i.e. the amount of Arabic gum in the material to be granulated is 100%.

As indicated above, the material to be granulated may comprise other substances, such as one or more metal salt(s) either alone or in combination with Arabic gum. If the material to be granulated comprises Arabic gum as well as other substances, such as one or more metal salt(s), the weight ratio between the other substances and Arabic gum in the material to be granulated may depend on the intended use of the granulate material obtained by the wet granulation process according to the present invention. For example, if the granulate material is intended for use as a dietary supplement for administering one or more metal salts, the ratio between such metal salt and the Arabic gum present in the material to be granulated may be dependent on the intended dose of the metal salt in the dietary supplement. For example, the amount of trace elements, such as zinc salts or selenium salts is typically less than the amount of other metal salts, such as calcium or magnesium salts.

Preferably, the weight ratio between the other substances and Arabic gum in the material to be granulated is between about 1:1 and about 1:500, preferably between about 1:1.5 and about 1:200, more preferably between about 1:2 and about 1:100, even more preferably between about 1:2 and about 1:50. For example, the material to be granulated may consist of 1 part other substances, such as an organic metal salt component, and 1 to 500 parts Arabic gum, e.g. depending on the intended use as set forth above.

In some embodiments, e.g. if calcium and/or magnesium salts are substances of the material to be granulated, the weight ratio between the other substances, e.g. the calcium and/or magnesium salts, and Arabic gum in the material to be granulated is preferably between about 1:1 and about 1:10, preferably between about 1:1.5 and about 1:8, more preferably between about 1:2 and about 1:6. For example, the material to be granulated may consist of 1 part organic metal salt component, such as a single organic metal salt, e.g. calcium gluceptate, or a combination of organic metal salts, such as a combination of organic magnesium, calcium and zinc salts, e.g. magnesium lactate, calcium gluceptate and zinc gluconate, and 2 to 4 parts Arabic gum.

In a preferred embodiment of the wet granulation process according to the present invention, the material to be granulated comprises, preferably consists of Arabic gum and an organic salt of calcium, such as calcium lactate, calcium gluconate, calcium gluceptate, calcium glutamate, preferably calcium gluceptate, wherein preferably the ratio between the other substances comprising or consisting of an organic calcium salt and Arabic gum is between about 1:2 and about 1:50, preferably between about 1:5 and about 1:30, even more preferably between about 1:2 and about 1:5, most preferably between about 1:3 and about 1:4.

In another preferred embodiment of the wet granulation process according to the present invention, the material to be granulated comprises, preferably consists of Arabic gum and an organic salt of magnesium, such as magnesium lactate, magnesium gluconate, magnesium gluceptate, magnesium glutamate, preferably magnesium lactate, wherein preferably the ratio between the organic magnesium salt and Arabic gum is between about 1:2 and about 1:30, preferably between about 1:3 and about 1:20, even more preferably between about 1:5 and about 1:6, most preferably between about 1:4 and about 1:6.

In a particularly preferred embodiment of the wet granulation process according to the present invention, the material to be granulated comprises, preferably consists of Arabic gum, an organic salt of magnesium, such as magnesium lactate, an organic salt of calcium, such as calcium lactate, calcium gluconate, calcium gluceptate, calcium glutamate, preferably calcium gluceptate, and an organic salt of zinc, such as zinc gluconate, wherein preferably the ratio between the organic metal salts and Arabic gum is between about 1:1.5 and about 1:50, preferably between about 1:2 and about 1:25, more preferably between about 1:1.5 and about 1:4, most preferably between about 1:2 and about 1:3, wherein the amounts of the individual organic metal salts may be dependent on an intended dose.

Depending on the amount of Arabic gum used in the granulating liquid for the wet granulation process the ratios of Arabic gum to other agents, such as one or more organic metal salts, in the end product, i.e. the granulate material obtained from the wet granulation process according to the present invention, may deviate from the ratio of the Arabic gum to other compounds in the material to be granulated. For example, if 10% of the total amount of Arabic gum is used in the granulating liquid, these 10% of Arabic gum will also be present in the end product.

In a preferred embodiment, the end product obtained by the wet granulation process according to the present invention, i.e. the granulate material obtained by the wet granulation process, comprises at least 5% Arabic gum, such as 8%, preferably at least 10% Arabic gum, more preferably at least 15% (w/w) Arabic gum, even more preferably at least 20% (w/w) Arabic gum. In a particularly preferred embodiment, the end product obtained by the wet granulation process according to the present invention, i.e. the granulate material obtained by the wet granulation process, comprises at least 40%, preferably at least 50%, more preferably at least 60%, even more preferably at least 70% Arabic gum.

By selecting suitable Arabic gum contents in the granulate material, granulating properties can generally be improved, while also the mechanical stability of the granulate material increases.

In a preferred embodiment, the process according to the present invention is characterized by the steps of
a. providing a predetermined amount of granulating liquid comprising Arabic gum, preferably a sprayable liquid,
b. providing a predetermined amount of material to be granulated, preferably a powder or powder mix,
c. optionally pre-warming the material to be granulated, preferably the powder,
d. contacting the granulating liquid of step a. with the material to be granulated of step b. or c., preferably by spraying the granulating liquid on to the material to be granulated.

The obtained granulate material may be dried during or after the granulation process, e.g. as described above. The process parameters such as amount of Arabic gum in the granulating liquid, the amount of granulating liquid and material to be granulated etc. are preferably as described above.

In a further aspect, the present invention provides a granulate material comprising Arabic gum. In the sense of the present invention, a "granulate material" is a conglomeration of discrete solid, preferably macroscopic particles. The discrete, solid particles of the granulate material are referred to herein as granules. The granules are preferably large enough such that they are not subject to thermal motion fluctuations. A granule in the sense of the present invention is preferably composed of agglomerated smaller particles such as agglomerated powder particles and/or agglomerated crystal particles. A granule in the sense of the present invention may, for example, be composed of agglomerated Arabic gum powder which serves as a matrix for one or more metal salt(s), preferably one or more organic metal salt(s), in the form of small crystalline particles, wherein the metal salt particles and the Arabic gum powder particles preferably exhibit material bonding between each other.

In the sense of the present invention, the granulate material is preferably obtainable by a granulation process using a powder material as starting material, i.e. using smaller particles to generate larger particles, the granules, by a granulation process such as by a wet granulation process as described herein.

Granulate material may be characterized by the parameter flow ability. For example, a granulate material in the sense of the present invention preferably exhibits flow ability in a Copley Scientific automatic flow-meter (e.g. Type BEP AUTO) with an orifice size of 1.5 cm, e.g. at a flow speed of at least 5 g/s such as between about 7 and 15 g/s. A powder material in the sense of the present invention preferably does not exhibit significant flow ability in such setting. Thus, for example, the parameter flow ability may be used to discriminate granulate material and powder material.

The individual granules of the granulate material according to the present invention are porous. That means that the individual granules, i.e. the discrete solid particles making up the granulate material, exhibit void spaces within the granules. Such void spaces may result from pores, fissures, rifts, pockets, inclusions etc.

The parameter characterizing the void spaces of the individual granules is termed "porosity". In the sense of the present invention, porosity preferably means the void volume in relation to the total volume of the granule, i.e. the fraction of the void volume in percent of the total volume of the granule. The porosity of the granules may, for example, be determined by analysing electron microscopic images of the granules or images of sections through the granules for void spaces (e.g. FIG. 17).

The void spaces, such as the pores, pockets or fissures, may be enclosed within the material making up the granule, which may be termed "unconnected porosity", or they may be connected to the surface of the granule, i.e. to the fluid surrounding the granule, which may be termed "connected porosity". It is preferred that both types of porosity exist in the granule, wherein an increased amount of connected porosity is particularly preferred. For example, it is preferred that at least a fraction of the pores or pockets located within the granule, such as at least 10%, preferably at least 20%, more preferably at least 30% of the pores or pockets, are connected to the surface of the granule, i.e. to the fluid (e.g. the air or solvent) surrounding the granule, for example by fissures or other pores.

The individual granules of the granulate material according to the present invention preferably exhibit a mean porosity of at least 15%, preferably of at least 20%, more preferably of at least 30%, even more preferably of at least 40%. In this context, "mean porosity" means the average porosity of the individual granules averaged over a number of individual granules making up the granulate material, for example over 10, 20, 30, 40, or 50 granules of the granulate material according to the present invention. Preferably, the porosity of the individual granules, preferably the mean porosity, is between about 15% to about 75%, preferably between about 20% to about 70%, more preferably between about 30% to about 60%. Preferably, at least 30% of the individual granules of the granulate material according to the present invention exhibit a porosity of at least about 20%, preferably of at least about 30%, more preferably of at least about 40%. Preferably, at least 40% of the individual granules of the granulate material according to the present invention exhibit a porosity of at least about 20%, preferably of at least about 50%, more preferably of at least about 40%.

The void spaces resulting in the porosity of the granules making up the granulate material of the present invention are preferably in the form of pores and fissures or channels. Preferably, a substantial fraction of the void volume, such as more than 50%, preferably more than 60%, more preferably more than 70% results from pores. The pores are preferably at least partially round, more preferably essentially round in shape, for example, the pores may exhibit an essentially globular or spherical shape. Thus, for example, at least 50% of the void volume of the granules making up the granulate material of the present invention may result from essentially round shaped pores (e.g. FIG. 17).

Preferably, the average pore diameter of the pores within the granules of the granulate material is between about 20 μm and about 80 μm, preferably between about 30 μm and about 70 μm, wherein the individual pore diameters preferably range up to about 150 μm, such as from about 5 μm to about 150 μm, preferably range up to 100 μm, such as from about 10 μm to about 100 μm.

The mean particle size or the median particle size (d50) of the granules making up the granulate material of the present invention is preferably in the range of 100 μm to about 800 μm, preferably in the range of about 200 μm to about 600 μm, more preferably in the range of about 300 μm to about 600 μm measured by sieving analysis. Preferably, the mean particle size and/or the median particle size (d50) of the granules making up the granulate material of the present invention is at least 200 μm, preferably at least 250 μm.

Regarding the particle size distribution, preferably, at least about 95%, more preferably at least about 98%, most preferably at least 99% of the granules of the granulate material according to the present invention exhibit a particle size of between about 50 μm and about 1000 μm, preferably between about 90 μm and about 800 μm. Preferably, at least 50% of the granules exhibit a particle size of between about 250 μm and about 710 μm. Preferably, at least 40% of the granules, more preferably at least 50% of the granules exhibit a particle size of between about 250 μm and about 500 μm. Preferably, less than 10%, more preferably less than 5% of the granules making up the granulate material according to the present invention exhibit a particle size of below 125 μm.

The particle size and particle size distribution in the sense of the present invention means the particle size and particle size distribution measured by sieving analysis. Thus, for example, the particle size of the granules making up the granulate material according to the present invention and the particle size distribution may be determined by using a sieving analysis or a graduation test apparatus, such as a Retsch AS 200. To this end, the granulate material is screened through a series of sieves having decreasing mesh widths, e.g. 2000 μm, 1400 μm, 1000 μm, 710 μm, 500 μm, 555 μm, 250 μm, 180 μm, 125 μm, and 90 μm. The mass of the residue on each sieve is determined and its fraction of the total granulate material mass applied to the sieving analysis is calculated in percent. The mean particle size is then calculated by methods known to the skilled person, for example, by using a Retsch AS 200 apparatus and determining the mean particle size, e.g. by the standards according to the European Pharmacopoeia (Ph.Eu.). The median particle size (d50) refers to the mass median diameter, which means that 50% of the particles by weight have a diameter (particle size) of less than d50 and 50% of the particles by weight have a diameter (particle size) of more than d50.

The shape of the granules of the granulate material according to the present invention is preferably irregular. This means preferably that the granules do not exhibit a regular shape such as a geometric shape, e.g. an essentially round or cubic shape as can be seen for some crystal structures for example. Rather, the granules are preferably rough and divers in shape. Preferably, the surface of the granules is rutted, preferably heavily rutted. In this context, "rutted" preferably means that the surface is not smooth and comprises, e.g. dents, bumps, buckles, furrows, grooves, rills, fissures, and/or channels. Preferably, pores within the granules are spatially connected with the surface of the granules, e.g. via the rills forming the rutted surface.

The granulate material according to the present invention exhibits improved dissolution kinetics, meaning increased dissolution speed, when compared, for example, to the material in ungranulated form, e.g. the material before granulation, such as in powder form. The dissolution speed of the granulated material is preferably increased by at least 2-fold, more preferably by at least 5-fold, even more preferably, by at least 5-fold compared to the ungranulated material.

Preferably, the granulate material according to the present invention completely dissolves in an aqueous solution (e.g. at about neutral pH) at a concentration of about 5% (w/v) with manual stirring at room temperature, e.g. at about 20° C. to 25° C. in less than 5 minutes, preferably in less than 3 minutes, more preferably in less than 1 minute, for example in about so seconds. "Manual stirring" preferably means stirring with a commonly used spoon at normal stirring speed. Preferably, the granulate material according to the present invention is completely dissolvable in 100 ml aqueous solvent, such as in water at about neutral pH, at a concentration of about 5% (w/v) at room temperature, e.g. at about 20° C. to 25° C., in less than 5 minutes, preferably in less than 3 minutes, more preferably in less than 1 minute, even more preferably in less than or about 30 seconds when stirred at 100 rpm using a conventional magnetic stirrer in a 200 ml beaker.

"Complete dissolution" means the material entering the dissolution test, e.g. the granulate material, is completely dissolved in the solvent, i.e. that no solid particles of undissolved particles remain. Complete dissolution may be determined by observing clearance of the solution, i.e. by observing disappearance of turbidity. In other words, dissolution may be assessed by assessing turbidity of the solution and dissolution speed may be assessed by measuring or observing the changes in turbidity over time. For example, when the solution is no longer turbid, complete dissolution has occurred.

The granulate material according to the present invention comprises Arabic gum. Preferably, the amount of Arabic gum in the granulate material is at least 5% (w/w), such as at least or about 8% (w/w), more preferably at least 20% (w/w), more preferably at least 40% (w/w), more preferably at least 50% (w/w), even more preferably at least 60% (w/w), even more preferably at least 80%, for example, about 64%, about 70%, about 75%, about 80%, about 84% etc.

The granulate material according to the present invention may even comprise Arabic gum in an amount of about 95%, 99% or 100% (w/w). Thus, in one embodiment, the granulate material according to the present invention essentially consists of Arabic gum. This means in the context of the present invention preferably that the only ingredient of the granulate material is Arabic gum apart from an optional residual moisture content. It is preferred that the quantities provided for the ingredients of the granulate material according to the present invention do not consider optional residual moisture content of the granulate material. Thus, preferably, the quantities are provided in relation to the total solid content of the granulate material ignoring an optional residual moisture content.

In one embodiment, the granulate material according to the present invention further comprises one or more other compounds, for example, metal salt(s), preferably one or more organic metal salt(s) as described above. Preferably, the metal is a monovalent or bivalent metal, for example, selected from the group consisting of potassium, sodium, lithium, calcium, magnesium, zinc, selenium, and iron. The counter ion of the metal salt is preferably an organic counter ion, for example, selected from the group consisting of acetate, alginate, ascorbate, aspartate, amygdalate, benzoate, borogluconate, carbasalate, carbonate, citrate, cyclamate, dinatriumtetralactate, dobesilate, ferro-phospholactate, folinate, formate, fumarate, glubionate, glucoheptonate, gluconate, glutamate, glycerophosphate, iopodate, ketoglutarate, lactate, lactogluconate, laevulinate, malate, methionate, orotate, oxalate, pangamate, pantothenate, phospholactate, phatalate, picrate, pidolate, propionate, resinate, saccharate (=glucarate), saccharin, sorbate, succinate, etc. For example, the organic counter ion is selected from the group consisting of lactate, gluceptate, glutamate, citrate, malate, pantothenate, acetate, gluconate and ascorbate. Preferred metal ion salts are lactate, such as magnesium lactate or calcium lactate, gluconate, such as calcium gluconate or zinc gluconate, gluceptate, such as calcium gluceptate, and glutamate, such as calcium glutamate. A particular preferred combination—if more than one metal salt is used—is the combination of a magnesium, a calcium and a zinc salt, such as a combination of magnesium lactate, calcium gluceptate and zinc gluconate.

The further compounds, such as the one or more metal salt(s) as described above, may, for example, be present in the granulate material according to the present invention in an amount of between 0% and 95% (w/w), preferably in an amount between 5% and 50% (w/w), more preferably in an amount of between 10% and 40%, even more preferably in an amount of between 10% and 30%, such as in an amount of about 15%, 20% or 25% (w/w).

As indicated above, the weight ratio between the other substances and Arabic gum in the granulate material may depend on the intended use. For example, if the granulate material is intended for use as a dietary supplement for administering one or more metal salts, the ratio between such metal salt and the Arabic gum present in the material to be granulated may be dependent on the intended dose of the metal salt in the dietary supplement. For example, the amount of trace elements, such as zinc salts or selenium salts is typically less than the amount of other metal salts, such as calcium or magnesium salts.

Preferably, the weight ratio between the other substances and Arabic gum in the granulate material according to the present invention is between about 1:1 and about 1:500, preferably between about 1:1.5 and about 1:200, more preferably between about 1:2 and about 1:100, even more preferably between about 1:2 and about 1:50. For example, the granulate material according to the present invention may consist of 1 part, other substances, such as one or more organic metal salts etc., and 1 to 500 parts Arabic gum, e.g. depending on the intended use as set forth above.

In some embodiments, e.g. if calcium and/or magnesium salts are substances of the material to be granulated, the weight ratio between the other substances, e.g. the calcium and/or magnesium salts, and Arabic gum in the granulate material according to the present invention is preferably between about 1:1 and about 1:10, preferably between about 1:1.5 and about 1:8, more preferably between about 1:2 and about 1:6. For example, the material to be granulated may consist of 1 part organic metal salt component, such as a single organic metal salt, e.g. calcium gluceptate, or a combination of organic metal salts, such as a combination of organic magnesium, calcium and zinc salts. e.g. magnesium lactate, calcium gluceptate and zinc gluconate, and 2 to 4 parts Arabic gum.

In a preferred embodiment, the granulate material according to the present invention comprises, preferably consists of Arabic gum and an organic salt of calcium, such as calcium lactate, calcium gluconate, calcium gluceptate, calcium glutamate, preferably calcium gluceptate, wherein preferably the ratio between the other substances comprising or consisting of an organic calcium salt and Arabic gum is between about 1:2 and about 1:50, preferably between about 1:3 and about 1:30, even more preferably between about 1:2 and about 1:5, most preferably between about 1:3 and about 1:4.

In another preferred embodiment, the granulate material according to the present invention comprises, preferably consists of Arabic gum and an organic salt of magnesium, such as magnesium lactate, magnesium gluconate, magnesium gluceptate, magnesium glutamate, preferably magnesium lactate, wherein preferably the ratio between the organic magnesium salt and Arabic gum is between about 1:2 and about 1:30, preferably between about 1:3 and about 1:20, even more preferably between about 1:3 and about 1:6, most preferably between about 1:4 and about 1:6.

In a particularly preferred embodiment, the granulate material according to the present invention comprises, preferably consists of Arabic gum, an organic salt of magnesium, such as magnesium lactate, an organic salt of calcium, such as calcium lactate, calcium gluconate, calcium gluceptate, calcium glutamate, preferably calcium gluceptate, and an organic salt of zinc, such as zinc gluconate, wherein preferably the ratio between the organic metal salts and Arabic gum is between about 1:1.5 and about 1:50, preferably between about 1:2 and about 1:25, more preferably between about 1:1.5 and about 1:4, most preferably between about 1:2 and about 1:5, wherein the amounts of the individual organic metal salts may be dependent on an intended dose.

In a preferred embodiment, the dissolution properties, such as achievable extent of dissolution and dissolution kinetics in an aqueous solvent, e.g. in water at approximately neutral pH, at room temperature of the one or more metal salts as described above is improved compared to the dissolution properties of the metal salt not formulated in the granulate material of the present invention. The improved dissolution kinetics of the metal salt in the granulate material according to the present invention may, for example, be determined using a dissolution tester, such as the Erweka Type DT600 instrument, in combination with a conductometer, such as the Metrohm 856 conductivity module. This analysis indicates dissolution of the metal salt by an increase in conductivity. The dissolution speed of the metal salt within the granulated material is preferably increased by at least 2-fold, more preferably by at least 3-fold, even more preferably, by at least 5-fold compared to the ungranulated metal salt.

The granulate material according to the present invention may contain a residual moisture content. The residual moisture content may, for example, result from the manufacturing process, e.g. from the wet granulation process. An optional moisture content of the granulate material is between about 1% and about 20% (w/w), preferably between about 2% and about 15% (w/w), more preferably between about 5% and about 12% (w/w). The moisture content of granulate material may, for example, be determined by a moisture content analysis apparatus, such as a Mettler Toledo HB43 apparatus.

The granulate material according to the present invention is preferably obtainable or obtained by the wet granulation process according to the present invention.

The granulate material according to the present invention is characterized by very good and quick dissolution kinetics and complete solubility. It provides for a readily obtainable solution of Arabic gum overcoming the problems concerning slow dissolution kinetics and incomplete dissolution of available Arabic gum preparations, e.g. in aqueous solvents such as water.

The granulate material according to the present invention is preferably suitable for preparing a liquid, preferably a drinkable liquid, such as a beverage. Thus, the present invention also provides the granulate material according to the present invention for preparing a liquid or gel, preferably a drinkable liquid or gel, such as a beverage, as well as a use of the granulate material according to the present invention for preparing a liquid or gel, preferably a drinkable liquid or gel, such as a beverage.

Furthermore, the present invention provides a composition comprising the granulate material according to the present invention. Preferably, the composition is for preparing a liquid or gel, preferably a drinkable liquid or gel, such as a beverage. In a preferred embodiment, the composition is a pharmaceutical composition, which contains further pharmaceutically active and/or pharmaceutically acceptable components. In a further preferred embodiment, the composition comprising the granulate material according to the invention is a cosmetic composition. It is preferred that the granulate material in the composition maintains the properties of the granulate material, e.g. the improved dissolution kinetics. In other words, the composition of the present invention is prepared in a manner in which the properties of the granulate material, e.g. the improved dissolution kinetics, are maintained.

The present invention further relates to the granulate material according to the present invention or the composition according to the present invention for use as a dietary supplement as well as to the use of the granulate material according to the present invention or the composition according to the present invention as a dietary supplement. In particular, a granulate material or a composition is provided for use as a dietary supplement in a clinical setting.

The present invention also provides the granulate material according to the present invention or the composition according to the present invention for use as a medicament. In a preferred embodiment, the granulate material according to the invention or the composition according to the invention is used as a medicament for the treatment of, for example, osteomalacia, chronic renal failure, diabetes, hypercholesterolemia, obesity, ulcerative colitis.

Preferably, the granulate material or the composition according to the present invention is for use in the treatment or prevention of deficiency symptoms, such as vitamin or mineral deficiency, in particular metal ion deficiency, such as iron, calcium, potassium, zinc and/or magnesium, selenium, lithium, or sodium deficiency.

The present invention further provides the granulate material according to the present invention and the composition according to the present invention for use in the treatment, amelioration or prevention of disorders or conditions amenable to treatment or prevention by metal ion supplementation, for example, by calcium, magnesium, potassium, iron, selenium, lithium, sodium and/or zinc supplementation.

For example, a granulate material according to the present invention comprising iron, such as an organic metal salt comprising iron as described above, or a composition comprising such granulate material may be used for preventing, ameliorating or treating iron deficiency and/or disorders or conditions associated with iron deficiency, such as chronic fatigue, weakness, dizziness, headaches, depression, sore tongue, sensitivity to cold (low body temperature), shortness of breath (when doing simple tasks, e.g. climbing stairs, walking short distances, doing housework), restless legs syndrome etc.

A granulate material according to the present invention comprising magnesium, such as an organic metal salt comprising magnesium, e.g. magnesium lactate, as described above, or a composition comprising such granulate material may be used, e.g. for preventing, ameliorating or treating magnesium deficiency and/or disorders or conditions associated with magnesium deficiency, such as mitral valve prolapse syndrome, migraine, attention deficit disorder, fibromyalgia, asthma, allergies, anxiety, psychiatric disorders, diabetes, kidney stones, hypertension, muscle cramps, constipation, chronic fatigue, cardiovascular disease, arrhythmia etc.

A granulate material according to the present invention comprising calcium, such as an organic metal salt comprising calcium, e.g. calcium gluceptate, as described above, or a composition comprising such granulate material may be used, e.g. for preventing, ameliorating or treating calcium deficiency and/or disorders or conditions associated with calcium deficiency, such as diseases associated with week bones, osteoporosis, high blood pressure, arthritis, poor sleep disorder, irritable nerves, allergies, such as allergic reactions against sun light etc.

A granulate material according to the present invention comprising potassium, such as an organic metal salt comprising potassium as described above, or a composition comprising such granulate material may be used, e.g. for preventing, ameliorating or treating potassium deficiency and/or disorders or conditions associated with potassium deficiency, such as hypokalemia, muscular weakness, myalgia, muscle cramps, flaccid paralysis, hyporeflexia etc.

A granulate material according to the present invention comprising zinc, such as an organic metal salt comprising zinc as described above, or a composition comprising such granulate material may be used, e.g. for preventing, ameliorating or treating zinc deficiency and/or disorders or conditions associated with zinc deficiency, such as hypozincemia, hair loss, skin lesions, diarrhea, and wasting of body tissues, appetite disorders, anorexia, cognitive and motor function impairment, pneumonia, acrodermatitis enteropathica, Dysmenorrhea, etc.

A granulate material according to the present invention comprising selenium, such as an organic metal salt comprising selenium as described above, or a composition comprising such granulate material may be used, e.g. for preventing, ameliorating or treating selenium deficiency and/or disorders or conditions associated with selenium deficiency, such as heart or cancer diseases, arthritis, hypothyroidism, acne, joint disease, psoriasis, extreme fatigue, mental slowing, goiter, cretinism, recurrent miscarriage, etc.

A granulate material according to the present invention comprising lithium, such as an organic metal salt comprising lithium as described above, or a composition comprising such granulate material may be used, e.g. for preventing, ameliorating or treating lithium deficiency and/or disorders or conditions associated with lithium deficiency, such as psychiatric diseases, depression, mood disorders, attention deficit spectrum disorders, etc.

A granulate material according to the present invention comprising sodium, such as an organic metal salt comprising sodium as described above, or a composition comprising such granulate material may be used, e.g. for preventing, ameliorating or treating sodium deficiency and/or disorders or conditions associated with sodium deficiency, such as hyponatremia, tiredness, disorientation, headache, muscle cramps, nausea, etc.

The present invention also provides a method for producing a beverage comprising the steps of dissolving the granulate material according to the present invention in a drinkable liquid or gel, preferably in an aqueous liquid, such as water. Furthermore, the present invention provides a beverage produced by said method.

Preferably, the soluble granulate manufactured according to the invention is mixed with a desired amount of liquid, for example by stirring, for obtaining a beverage. Such beverage may be used for administration of a defined amount of an active agent to the body of an individual. E.g. the individual may be supplemented with Ca, K, Mg, Zn, Fe or any other metal in need by drinking this beverage. Accordingly, the invention relates further to a method of production of a beverage comprising the step of dissolving the granulate material according to the present invention in a predetermined amount of a liquid. This method preferably comprises the steps of
   a. optionally, producing a granulate material using the method according to the invention,
   b. dissolving the soluble granulate in a predetermined volume of a liquid.

Beverages containing Arabic gum are particularly advantageous due to the good properties of Arabic gum with respect to bio-compatibility and the further function of Arabic gum as a dietary fiber. Accordingly, a further embodiment of the invention relates to a beverage produced according to the invention. Such beverage may be used in prophylaxis and treatment of nutrient-deficiencies, particularly for use in prophylaxis and treatment of Ca-deficiency, Mg-deficiency, Zn-deficiency, K-deficiency, Se-deficiency, Li-deficiency, Na-deficiency and/or Fe-deficiency.

A granulate material comprising Arabic gum as a matrix agent according to the present invention may be used with advantage for providing solutions containing precisely defined doses of effective agents, e.g. of mono- or bivalent metal ions for supplementation of a healthy diet.

In case the granulate material is to be used for providing an edible liquid, a further advantage of the invention is that the body may absorb metal ions, e.g. Ca-ions with strikingly higher efficiency from such a liquid than from pure Ca-solutions. Thus, Arabic gum contained within the granulate material according to the present invention assists proper absorption of the contained active agent. In other words, the Arabic gum contained within the granulate material according to the invention may act as a carrier for a metal salt, e.g. and organic metal salt, to be administered. Furthermore, granulate material essentially consisting of Arabic gum may be used for increasing the uptake of nutrients such as metal ions from food. Thus, if granulate material according to the present invention essentially consisting of Arabic gum is consumed together with normal food, the nutrients of the food will be taken up more efficiently by the body. Furthermore, the treated individual may benefit form the Arabic gum as dietary fiber, further supporting nutrition.

A further advantage of the invention is that Arabic gum mediates solubility of active agents, such as certain salts, that are per se well suitable for food supplementation, e.g. Ca-Phosphates or the like, but exhibit only very low solubility. The granulate material produced according to the method of the invention may help to overcome this low solubility by mediating the solution of these salts, preferably in aqueous solvents. Thus, the present invention provides a method for improving solubility or dissolution kinetics of an active agent, such as a metal salt, e.g. an organic metal salt as described above, preferably in aqueous solvents, the method comprising the wet granulation process according to the present invention as described above, wherein the material to be granulated comprises the active agent, e.g. the metal salt as described above.

In particular, the process and the granulate material according to the invention can advantageously be used in the cosmetic industry. Specifically, the granulate according to the invention or the composition according to the invention can be applied in cosmetic products, which contain further cosmetically active and/or cosmetically acceptable components, such as ointments, creams, lotions, oils, foams, gels, shampoos, powders, lacquers, brilliantines. Preferably, the granulate according to the invention or the composition according to the invention is used in a sunscreen.

The wet granulation process and the granulate material according to the present invention are also useful for other industrial applications than food or pharmaceutical or cosmetic industries. For example, the present invention provides advantages in the production of dyes, inks and paints, particularly pigment paints or inks. Inks or paints containing pigments, such as Pigment Black 7 or Indian Yellow, are known to provide particularly good color stability. Such pigments, however, require the use of emulsifying agents to be usable in liquid form. Such emulsifying agent may be provided in form of the granulate material according to the invention. Accordingly, the material to be granulated may also comprise a pigment, e.g. for an ink, paint or dye. For example, in the method according to the present invention, the material to be granulated may comprise one or more pigments, e.g. useful for the production of inks, dyes or paints. Thus, the present invention also provides the use of the granulate material according to the present invention for the production of dyes, inks or paints. Furthermore, in the present invention relates to a method for producing a dye, paint or ink comprising the steps a. production of a granulate material using the method according to the present invention, wherein the material to be granulated comprises one or more pigments, and b. dissolving the granulate material in a predetermined volume of a liquid, as well as to a dye produced according to this method. Such dyes are advantageous, particularly, due to the non-toxicity of Arabic gum. In addition, the process according to the invention or the granulate material according to the invention is useful for manufacturing matches as well as ceramic products.

Accordingly, the granulate material produced by the method according to the invention may be added to a liquid, semi-liquid or gel-like carrier in order to provide, e.g. a drinkable gel or liquid, a liquid pigment dye or an ink.

A granulate material as obtained by the present invention may be aliquoted into predetermined package sizes. Such aliquots are storable for a long time and can be used separately from each other, e.g. each as a single dose. For application of the produced soluble granulate one or more packages simply may be stirred into a predetermined volume of liquid. The soluble granulate according to the invention dissolves quickly and completely in aqueous solvents, yielding a homogenous solution without clumping or formation of agglomerates.

Taken together, the present invention provides several advantages such as improved solubility and dissolution kinetics of Arabic gum and active agents, such as metal salts, improved storage stability and easy processing and handling of Arabic gum containing compositions.

Further details and characteristics of the invention may be recognized from the following Figures and Examples.

FIGURES

FIG. 1 shows an electron micrograph of a granulate material according to the present invention consisting of Arabic gum and calcium lactate (about 86% Arabic gum). The upper panel represents a 200× magnification, scale bar=500 µm. The lower panel represents a 500× magnification, scale bar=200 µm.

FIG. 2 shows an electron micrograph of a granulate material according to the present invention consisting of Arabic gum and calcium glutamate (about 82% Arabic gum). The upper panel represents a 20× magnification, scale bar=500 µm. The lower panel represents a 500× magnification, scale bar=200 µm.

FIG. 3 shows an electron micrograph of a granulate material according to the present invention consisting of Arabic gum and magnesium lactate (about 84% Arabic gum). The upper panel represents a 200× magnification, scale bar=500 µm. The lower panel represents a 500× magnification, scale bar=200 µm.

FIG. 4 shows an electron micrograph of a granulate material according to the present invention consisting of Arabic gum and zinc gluconate (about 99% Arabic gum). The upper panel represents a 200× magnification, scale bar=500 µm. The lower panel represents a 500× magnification, scale bar=200 µm.

FIG. 5 shows an electron micrograph of a granulate material according to the present invention consisting of Arabic gum, magnesium lactate, calcium gluceptate and zinc gluconate (cf. Example 6a, multi-batch 1/5, about 75% (w/w) Arabic gum). The upper panel represents a 200× magnification, scale bar=500 µm. The lower panel represents a 500× magnification, scale bar=900 µm.

FIG. 6 shows an electron micrograph of a granulate material according to the present invention consisting of Arabic gum, magnesium lactate, calcium gluceptate and zinc gluconate (cf. Example 6b, multi-batch 1/3, about 65% Arabic gum). The upper panel represents a 200× magnification, scale bar=500 µm. The lower panel represents a 500× magnification, scale bar=200 µm.

FIG. 7 shows an electron micrograph of a single granule of the granulate material according to the present invention consisting of Arabic gum and magnesium lactate (cf. Example 3 as described below, about 84% Arabic gum). The image is a 150× magnification, scale bar=100 µm.

FIG. 8 shows an electron micrograph of a single granule of the granulate material according to the present invention essentially consisting of Arabic gum (cf: Example 1 as described below, 100% Arabic gum). The image represents a 75× magnification, scale bar=100 µm.

FIG. 9 depicts the results of a dissolution assay providing the dissolution kinetics of the granulate material according to the present invention in comparison to ungranulated material measured by an increase in conductivity (Example 1: granulated Arabic gum; Example 2: granulated Arabic gum calcium gluceptate material, about 79% Arabic gum; Example 5: granulated Arabic gum magnesium lactate material, about 84% Arabic gum; Example 4: granulated calcium gluceptate Arabic gum material, about 8% Arabic gum; Example 5b: powder mix of ungranulated Arabic gum powder and calcium gluceptate, about 79% Arabic gum; Example 5c: powder mix of ungranulated Arabic gum powder and magnesium lactate, about 84% Arabic gum).

FIG. 10 depicts the results of a flow assay using a Copley Scientific automatic flow meter at an orifice size of 1.5 cm determining the flow properties of the samples shown in FIG. 9.

FIG. 11 shows bar diagrams of particle size distributions determined by sieving analysis using the Sieve analyzer "Retsch AS 200 control". The upper panel shows the particle size distribution of the powder mix of Arabic gum and calcium lactate before application to the granulation process according to the present invention. The bottom panel shows the particle size distribution of the granulated material according to the present invention consisting of Arabic gum and calcium lactate; about 86% Arabic gum.

FIG. 12 shows bar diagrams of particle size distributions determined by sieving analysis using the Sieve analyzer "Retsch AS 200 control". The upper panel shows the particle size distribution of the powder mix of Arabic gum and calcium glutamate before application to the granulation process according to the present invention. The bottom panel shows the particle size distribution of the granulated material according to the present invention consisting of Arabic gum and calcium glutamate; about 82% Arabic gum.

FIG. 13 shows bar diagrams of particle size distributions determined by sieving analysis using the Sieve analyzer "Retsch AS 200 control". The upper panel shows the particle size distribution of the powder mix of Arabic gum and magnesium lactate before application to the granulation process according to the present invention. The bottom panel shows the particle size distribution of the granulated material according to the present invention consisting of Arabic gum and magnesium lactate; about 84% Arabic gum.

FIG. 14 shows bar diagrams of particle size distributions determined by sieving analysis using the Sieve analyzer "Retsch AS 200 control". The upper panel shows the particle size distribution of the powder mix of Arabic gum and zinc gluconate before application to the granulation process according to the present invention. The bottom panel shows the particle size distribution of the granulated material according to the present invention consisting of Arabic gum and zinc gluconate; about 99% Arabic gum.

FIG. 15 shows bar diagrams of particle size distributions determined by sieving analysis using the Sieve analyzer "Retsch AS 200 control". The upper panel shows the particle size distribution of the powder mix of Arabic gum, magnesium lactate, calcium gluceptate and zinc gluconate before application to the granulation process according to the present invention. The bottom panel shows the particle size distribution of the granulated material according to the present invention consisting of Arabic gum magnesium lactate, calcium gluceptate and zinc gluconate (Multi-batch 5/1); about 75% Arabic gum.

FIG. 16 shows bar diagrams of particle size distributions determined by sieving analysis using the Sieve analyzer "Retsch AS 200 control". The upper panel shows the particle size distribution of the powder mix of Arabic gum, magnesium lactate, calcium gluceptate and zinc gluconate before application to the granulation process according to the present invention. The bottom panel shows the particle size distribution of the granulated material according to the present invention consisting of Arabic gum magnesium lactate, calcium gluceptate and zinc gluconate (Multi-batch 3/1); about 65% Arabic gum.

FIG. 17 shows electron micrographs of individual granule sections used for the determination of the porosity of the individual particles. The scale bar represents 100 µm.

FIGS. 1 to 6 demonstrate the irregular, rutted and rugged shape of the granules making up the granulate material according to the present invention. The higher magnification images also demonstrate the open porous structure of the granules (see also FIG. 17).

FIGS. 7 and 8 show individual granules 10 of Arabic gum (GA) having a rugged and/or irregular surface is making up the granulate material according to the present invention. Furthermore, the individual granules incorporate pores 14 and cavities 15. Such pores and cavities or cracks may be connected to build a connected void space within the granule.

If an active agent, e.g. an organic salt such as Mg-lactate, is used, grains or crystals of the organic salt 12 may be connected to Arabic gum GA by material bonding, as can be seen from FIG. 7. The organic salt grains 12 are at least partially incorporated into the granule 10. In other words, the matrix agent Arabic gum (GA) forms a matrix 11 containing grains of the effective agent, here: Mg lactate.

The granules depicted in FIG. 7 and FIG. 8 have a particle size of about 500 µm. They are produced by the method according to the invention comprising contacting the material to be granulated, e.g. Arabic gum and magnesium lactate (FIG. 7) or only Arabic gum (FIG. 8) in powder form with a granulating liquid comprising Arabic gum in solution. The granulating liquid has been sprayed on to the powder to be granulated in a fluidized bed granulation set up.

EXAMPLES

Wet Granulation Process

The material to be granulated has been prepared for the wet granulation process by weighing the desired amount of the components of the material to be granulated into an appropriate vessel and mixing the components. In general, commercially available Arabic gum powder (prepared by spray drying or dispersion desiccatum Arabic gum Ph.Eu., e.g. Sigma-Aldrich, CAS-number 9000-01-5) has been used as starting material. Optionally, metal salts, such as magnesium lactate, calcium gluceptate, calcium lactate, calcium glutamate, calcium gluconate and/or zinc gluconate in crystalline form have optionally been added to the Arabic gum powder. Metal salts that have been used are, for example, calcium α-D-heptagluconate (Sigma-Aldrich, CAS-number: 17140-60-2), calcium-L-lactate pentahydrate (Sigma-Aldrich, CAS-number: 5743-47-5), calcium-L-glutamate tetrahydrate (Sigma-Aldrich, CAS-number: 19238-49-4), magnesium L-lactate hydrate (Sigma-Aldrich, CAS-number: 18917-93-6), and zinc gluconate (Merck, CAS-number: 4468-02-4). Mixing of the components of the material to be granulated (dry solids such as powders and crystals) has been performed using a Turbula mixer (WAB Type Z2F) without mixing and chopping blades to generate a homogenous mixture of the materials to be granulated.

The granulating liquid has been prepared by dissolving Arabic gum in distilled water, for example, dissolving 50 g of Arabic gum in distilled water to prepare a 25% (w/v) solution of Arabic gum, i.e. adjusting the volume to 200 ml. Arabic gum has been added stepwise to the distilled water, while stirring gently avoiding the formation of undesired air bubbles within the solution. Furthermore, gentle and stepwise addition of Arabic gum to the total amount of water decreases the solution time. Optionally, 0.1 to 0.5% (w/w) (from total formulation weight) aroma have been added to the granulating liquid after complete dissolution of the Arabic gum.

After preparation of the material to be granulated (powder mix) and the granulating liquid both components have been processed by granulation within a fluidized bed set-up (Fluidized bed granulator GLATT GPC2 Labsystem) according to the following protocol:
 preheating the tower of the fluid bed set-up to approximately 40° C. before pouring the powder mixture into the granulation tower of the set-up;
 operating the granulator for a few minutes (such as 5 minutes) without spraying to let the powder reach the same temperature as the flow air;
 spraying the solution with a moderate spray rate (for example, a spray rate setting of 8 of the GLATT GPCG2 Labsystem granulator has been used for 5-6 minutes) in order for the first granulation layers to form and dry;

optionally, increase the tower's volume flow to let the solid content flow easily and dry properly;

increase the spray rate gradually to increase the particle size, if desired (for example, the spray rate setting has been adjusted from 8 to 10 after 5 to 6 minutes spraying and then to 12 after about 10 to 12 minutes spraying);

the product temperature has been controlled to be between 30° C. and 35° C. by increasing/decreasing the "inlet temperature";

the granulate material has been kept in the fluidized bed setting after spraying for a few minutes, for example five to ten minutes, for decreasing the product moisture content. Optionally or additionally drying may also be performed within a drying cabinet. A longer drying time will decrease the particle size of the end product.

Determination of Dissolution Kinetics

After manufacturing of the granulate material according to the previously described method, the dissolution kinetics of the granulate material in water has been analyzed. To this end, a certain amount of the product (10 to 12.6 g of granulate material) has been dissolved in 200 ml water. It has been determined by optical control if the granulate material dissolves, wherein disappearance of turbidity represents dissolution of the granulate material. The dissolution time has been recorded.

In addition to the manual and optical determination of dissolution properties of the obtained product, the release of ions into the solution has been measured for monitoring the dissolution of the metal salts contained in the granulate material. This measurement has been performed using Erweka type DT600 dissolution tester applying a paddle speed of 100 rpm and a Metrohm 856 Conductivity Module at room temperature (25° C.). Granulate material has been added to water to reach a concentration of 6.3% (w/w). The mixture has been stirred at 100 rpm for so Minutes. During this time, conductivity of the solution has been measured.

It can be seen from FIG. 9 that samples of granulate material containing Arabic gum as matrix agent that are manufactured according to the invention (Examples 1, 2, 3 and 4) dissolve very quickly and completely. However, control materials only dissolve partially (Examples 5b and 5c). Particularly, the material of Example 1 represents a granulate material essentially consisting of Arabic gum, i.e. without addition of other compounds such as organic metal salts. This sample (Example 1) has been prepared by spraying a liquid fraction containing 25% (w/v) Arabic gum over a powder consisting of Arabic gum and subsequently drying the obtained granulate material as described herein. A similar process has been applied to obtain granulate material samples 2, 3 and 4 (Examples 2, 3 and 4). They only differ by the particular composition of the material to be granulated, i.e. the powder mix. This means the granulate material of Examples 1, 2, 3 and 4 are prepared by a method according to the invention as described above. It can be seen from FIG. 9 that the granulate material according to the present invention (samples 1, 2, 3 and 4) exhibits increased dissolution kinetics, i.e. an increased dissolution speed, shown by rapid increase of conductivity after addition of the material to the solvent. This level of conductivity is maintained at about the same level over the time period of the experiment of about so minutes indicating that the granulate material has dissolved completely after the first few seconds of the experiment.

In contrast, a powder mixture of Arabic gum and an organic salt without granulation exhibits only a very slow increase of conductivity, as is demonstrated by Examples 5b and 5c in FIG. 9. Although these controls (Examples 5b and 5c) contain the same mixture of matrix agent and organic salts as Examples 2 and 3, it can be clearly seen that the materials of Examples 5b and 5c do not achieve the same level of conductivity as the granulate material of Examples 2 and 3, respectively, indicating incomplete dissolution and slow dissolution.

Analysis of the Flow Ability

For further characterization of the product obtained by the method of the invention, the flow properties of the granulate material has been tested. For measurements of the flow properties a Copley Scientific automatic flow meter has been used with an orifice size of 1.5 cm (Copley Scientific Limited, Colwick Quays Business Park, Private Road No. 2, Colwick, Nottingham, NG4 2JY, United Kingdom). The flow ability of a granulate material or powder may be defined within this context as to be the ability of the powder or granulate material, respectively, to flow through an opening (orifice) of a conical shape hopper. By this definition, flow ability can be understood as a one-dimensional characteristic of a powder/granulate material, whereby powders or granulate materials can be ranked on a sliding scale from free-flowing to non-flowing. For determining the flow properties, the granulate materials of Examples 1, 2, 3 and 4 produced according to the present invention as well as the control materials of Examples 5a, 5b and 5c all have been applied to the flow ability analyzing instrument. To this end, approximately 100 g of the respective test material have been weighed into the conical shape hopper for every experiment. The experiment was repeated three times for each sample.

It can be seen from the Table in FIG. 4 that granulate material manufactured according to the present invention (Examples 1, 2, 5 and 4) flows with an average speed of around 9.8 g/s through an orifice with an opening size of 1.5 cm while the powder mixtures of Examples 5a, 5b and 5c do not flow at all. This indicates a particular advantage of the granulate material according to the invention with respect to handling of the material. e.g. packaging and emptying a package before usage of the granulate material.

Determination of Particle Size and Particle Size Distribution

The particle size and particle size distribution of the starting material, i.e. the powder mixtures of Arabic gum and optionally an effective agent such as an organic metal salt, as well as the granulate material according to the present invention has been determined by sieving analysis using a "Retsch AS 200 control" sieve analyzer. The results of the sieving analysis are illustrated in FIGS. 11 to 16.

For example, the calcium lactate containing Arabic gum granulate material manufactured according to the present invention as well as the unprocessed starting material, i.e. the powder mix of Arabic gum and calcium lactate has been applied to the Retsch AS 200 control sieve analyzer. This analyzer comprises 10 sieve bottoms with decreasing mesh width, i.e. 2000 μm, 1400 μm, 1000 μm, 710 μm, 500 μm, 555 μm, 250 μm, 180 μm, 125 μm and 90 μm. The material remaining between the different sieve bottoms is weighed and the fraction of the sieve residue for each sieve bottom is calculated in %. The residue per mean mesh width is calculated in % and the mean particle size as well as the particle size distribution is determined as shown in tables 1 and 2 below. The mean particle size (provided in the last row of the last column of the Table) is determined using the standards according to the European Pharmacopoeia (Ph.Eu.).

TABLE 1

Sieve analysis raw data for granulate material comprising Arabic gum and calcium lactate. A mean particle size of 368.3 μm has been determined using the standards according to Ph. Eu. (FIG. 11 bottom panel).

| mesh width [μm] | Log mesh width [μm] | Mean mesh width x̄ [μm] | sieve residue [g] | sieve residue [%] | cumulative residue [%] | cumulative passaged material [%] | residue R pro x̄ [%] | x̄ · R / 100 [μm] |
|---|---|---|---|---|---|---|---|---|
| 2000 | 3.30 | 1700 | 0 | 0.00 | 0.00 | 100.00 | | |
| 1400 | 3.15 | 1200 | 0.06 | 0.06 | 0.06 | 99.94 | 0.06 | 1.0 |
| 1000 | 3.00 | 855 | −0.04 | −0.04 | 0.02 | 99.98 | −0.04 | −0.5 |
| 710 | 2.85 | 605 | 0.37 | 0.37 | 0.39 | 99.61 | 0.37 | 3.2 |
| 500 | 2.70 | 427.5 | 17.7 | 17.74 | 18.13 | 81.87 | 17.74 | 107.3 |
| 355 | 2.55 | 302.5 | 30.78 | 30.85 | 48.98 | 51.02 | 30.85 | 131.9 |
| 250 | 2.40 | 215 | 26.32 | 26.38 | 75.36 | 24.64 | 26.38 | 79.8 |
| 180 | 2.26 | 152.5 | 14.48 | 14.51 | 89.88 | 10.12 | 14.51 | 31.2 |
| 125 | 2.10 | 107.5 | 8.1 | 8.12 | 98.00 | 2.00 | 8.12 | 12.4 |
| 90 | 1.95 | 45 | 1.75 | 1.75 | 99.75 | 0.25 | 1.75 | 1.9 |
| Bottom | 1.80 | Total | 0.25 | 0.25 | 100.00 | 0.00 | 0.25 | 0.1 |
| | | | 99.77 | 100 | | | Σ | 368.3 |

TABLE 2

Sieve analysis raw data for powder mix comprising Arabic gum and calcium lactate, starting material for granulation process. A mean particle size of 137.9 μm has been determined using the standards according to Ph. Eu. (FIG. 11 upper pannel).

| mesh width [μm] | Log mesh width [μm] | Mean mesh width x̄ [μm] | sieve residue [g] | sieve residue [%] | cumulative residue [%] | cumulative passaged material [%] | residue R pro x̄ [%] | x̄ · R / 100 [μm] |
|---|---|---|---|---|---|---|---|---|
| 2000 | 3.30 | | 0 | 0.00 | 0.00 | 100.00 | | |
| 1400 | 3.15 | 1700 | 0.04 | 0.04 | 0.04 | 99.96 | 0.04 | 0.7 |
| 1000 | 3.00 | 1200 | 0.1 | 0.10 | 0.14 | 99.86 | 0.10 | 1.2 |
| 710 | 2.85 | 855 | 0.17 | 0.17 | 0.31 | 99.69 | 0.17 | 1.5 |
| 500 | 2.70 | 605 | 0.54 | 0.54 | 0.85 | 99.15 | 0.54 | 3.3 |
| 355 | 2.55 | 427.5 | 2.94 | 2.95 | 3.80 | 96.20 | 2.95 | 12.6 |
| 250 | 2.40 | 302.5 | 9.28 | 9.31 | 13.11 | 86.89 | 9.31 | 28.2 |
| 180 | 2.26 | 215 | 9.09 | 9.12 | 22.24 | 77.76 | 9.12 | 19.6 |
| 125 | 2.10 | 152.5 | 18.77 | 18.83 | 41.07 | 58.93 | 18.83 | 28.7 |
| 90 | 1.95 | 107.5 | 24.95 | 25.04 | 66.10 | 33.90 | 25.04 | 26.9 |
| Bottom | 1.80 | 45 | 33.78 | 33.90 | 100.00 | 0.00 | 33.90 | 15.3 |
| | | Total | 99.66 | 100 | | | Σ | 137.9 |

Mean particle sizes and median particle sizes (d50) of the granules making up the granulate material according to the present invention and the powder mix material as starting material of the granulation process are summarized in Table 3.

TABLE 3

Summary of the mean particle sizes and median particle sizes (d50).

| Material | Mean particle size [μm] | Median particle size (d50) [μm] |
|---|---|---|
| powder mix: GA + Ca-lactate | 109.8 | 94.6 |
| Granulate material: GA + Ca-lactate | 368.3 | 349.4 |
| powder mix: GA + Ca-glutamate | 137.9 | 111.0 |
| Granulate material: GA + Ca-glutamate | 305.8 | 288.9 |
| powder mix: GA + Mg-lactate | 102.5 | 87.7 |
| Granulate material: GA + Mg-lactate | 374.0 | 360.4 |
| powder mix: GA + Zn-gluconate | 97.2 | 86.4 |
| Granulate material: GA + Zn-gluconate | 391.5 | 392.9 |
| powder mix: GA + multi 1/5 | 108.7 | n.d. |
| Granulate material: GA + multi 1/5 | 359.1 | n.d. |
| powder mix: GA + multi 1/3 | 93.7 | n.d. |
| Granulate material: GA + multi 1/3 | 335.1 | n.d. |

Determination of Porosity

For the determination of the void volume, i.e. the porosity, within the individual granules of the granulate material according to the present invention, several electron micrographs of slices of individual granules have been analyzed for void volume in relation to the total volume of the granule. Some examples of electron micrographs that have been analyzed regarding porosity of individual granules are shown in FIG. 17. The following porosities (fraction of void volume in relation to total volume of the granule) have been estimated for the granules shown in the electron micrographs of FIG. 17: left upper panel: 40.5%, right upper panel: 63.7%, left bottom panel: 36.7%, right bottom panel: 45.7%.

Example 1: Granulate Material Essentially Consisting of Arabic Gum 500 g of Arabic gum powder (Sigma-Aldrich, CAS-number 9000-01-5) have been applied to the wet granulation process according to the present invention. No additional agents, such as metal salts, have been used.

90% of the starting material, i.e. 450 g, have been used as material to be granulated (in dry powder form) and 10%, i.e. 50 g, of Arabic gum have been in dissolved distilled water to obtain a volume of 200 ml and thus a 25% (w/v) solution, the granulating liquid as described above.

Dissolution, Optical Analysis:

For optical analysis of the dissolution properties of the obtained granulate material, 10 g have been dissolved in 200 ml deionized water. Dissolution has been determined by optical assessment of turbidity. Complete dissolution indicated by disappearance of turbidity has been observed after 28 seconds of manual stirring at room temperature.

Dissolution Property, Release of Ions:

In addition to manual dissolution and optical analysis described above, the release of ions in the solution was measured using Erweka type DT600 dissolution tester and Metrohm 856 Conductivity Module at room temperature as described above. It has been attempted to dissolve the product in the same manner and way which has to be done by product users in the future, which means adding the product in water or other beverages, mix and then drink. Therefore, 40.0 g granulate material has been added to 800 ml water to reach the desired mass concentration (w/w). The granulate material dissolved within the first few minutes.

It can be seen from FIG. 9 that conductivity of above 1.000 mS/cm has been achieved after a few minutes of dissolution. After reaching this level of conductivity, conductivity remained constant over the following period of measurement of about 30 minutes. This shows that after the first increase of the conductivity level, the whole amount of 4.0 g of the granulate material has been dissolved in water.

Flow Property:

Flow property has been analyzed as described above. It can be seen from Table 1 shown in FIG. 10 that granulate material of Example 1 flows with an average speed of 7.47 g/s through an orifice of 1.5 cm. Flow properties were measured three times. By a first measurement 99.9 g of granulates according to Example 1 needed 15.4 s for flowing through the orifice which means a speed of 7.45 g/s. By the second measurement 99.5 g of granulates were flowing through the orifice during 13.3.5 s corresponding to a speed of 7.44 g/s. While in a third measurement 100.0 g of granulates were flowing within 15.28 s through the orifice, corresponding to a speed of 7.53 g/s.

Example 2: Granulate Material of Arabic Gum and Calceptate

A total amount of 500 g of Arabic gum have been used as matrix agent. 129.1 g of Calcium gluceptate have been used as an organic metal salt.

The material to be granulated has been prepared by weighing of 90% the total Arabic gum, i.e. 450 g, into a proper vessel. These 450 g of Arabic gum have been mixed with 129.1 g calcium gluceptate salt in a proper mixer (without mixing and chopping blades, i.e. using a turbular mixer as described above) for approximately 10 minutes to ensure mixture homogeneity.

The remaining 10%. i.e. 50 g, of Arabic gum have been dissolved in a required amount of distilled water in order to obtain a 25% (w/v) solution. The granulation process has been performed as described above.

Dissolution, Optical Analysis:

For optical analysis of the dissolution properties of the obtained granulate material, 12.6 g (79.4% w/w Arabic gum, 20.6% w/w calcium gluceptate) have been dissolved in 200 ml deionized water by manual stirring at room temperature. Complete dissolution, indicated by disappearance of turbidity, has been observed after 29 seconds of manual stirring.

Dissolution Property, Release of Ions:

In addition to manual dissolution and optical analysis described above, the release of ions in the solution was measured using Erweka type DT600 dissolution tester and Metrohm 856 Conductivity Module at room temperature. 50.4 g of the granulate material have been added to 800 ml water to reach the desired mass concentration (w/w). The granulate material dissolved within the first few minutes.

It can be seen from FIG. 9 that a conductivity of more than 4,000 mS/cm has been achieved after a few minutes. After reaching the final level of conductivity of above 4.500 mS/cm after some more minutes, conductivity remained constant over the following period of measurement of about so minutes. This means: after the first increase of the conductivity the whole amount of 50.4 g of the granulate material has been dissolved in water.

Flow Property:

Flow property has been analyzed as described above. It can be seen from Table 1 shown in FIG. 10 that granulate material according to Example 2 flows with an average speed of 10.46 g/s through an orifice of 1.5 cm. Flow properties have been measured three times. During a first measurement, 99.7 g of granulate material according to Example 2 needed 9.51 s for flowing through the orifice which means a speed of 10.48 g/s. During a second measurement 99.5 g of granulate material has been flowing through the orifice during 9.55 s corresponding to a speed of 10.44 g/s. While in a third measurement 99.1 g of the granulate material has been flowing within 9.48 s through the orifice, corresponding to a speed of 10.45 g/s.

Example 3: Aggregate Granulates of Arabic Gum and Magnesium Lactate

A total amount of 500 g of Arabic gum as described above have been used as matrix agent. 98.1 g of magnesium lactate have been used as an effective agent.

The material to be granulated has been prepared by weighing of 90% of the total Arabic gum, i.e. 450 g, into a proper vessel. These 450 g of Arabic gum have been mixed with 98.1 g magnesium lactate salt in a proper mixer (without mixing and chopping blades, i.e. turbular mixer as described above) for approximately 10 minutes to ensure mixture homogeneity.

The remaining 10%. i.e. 50 g, of Arabic gum have been dissolved in an appropriate amount of distilled water in order to achieve a 25% (w/v) solution. The wet granulation process has been performed as described above.

Dissolution, Optical Analysis:

For optical analysis of the dissolution properties of the obtained granulate material, 12.0 g (85.3% m/m Arabic gum, 16.7% m/m magnesium lactate) have been dissolved in 200 ml deionized water. Complete dissolution, indicated by disappearance of turbidity, has been observed after 28 seconds of manual stirring at room temperature.

Dissolution Property, Release of Ions:

In addition to the manual dissolution and optical analysis described above, the release of ions in the solution has been measured using Erweka type DT600 dissolution tester and Metrohm 856 Conductivity Module at room temperature. 48 g of the granulate material of Example 3 have been added to 800 ml water to reach the desired mass concentration (w/w). The granulate material dissolved within the first few minutes indicated by a plateau reached in conductivity.

It can be seen from FIG. 9 that a conductivity of about 3,000 mS/cm has been achieved after a few minutes. After reaching this level of conductivity, conductivity remained constant over the following period of measurement of about 50 minutes. This means: after the first increase of the conductivity, the whole amount of 48 g of the granulate material has been dissolved in the water.

Flow Property:

Flow property has been analyzed as described above. It can be seen from Table 1 shown in FIG. 10 that granulate material according to Example 3 flows with an average speed of 11.61 g/s through an orifice of 1.5 cm. Flow properties have been measured three times wherein a first measurement 97.8 g of granulate material according to Example 3 needed 8.43 s for flowing through the orifice which means a speed of 11.60 g/s. The second measurement 99.5 g of granulate material have been flowing through the orifice during 8.57 s corresponding to a speed of 11.61 g/s through the orifice. While in a third measurement 99.9 g of granulate material have been flowing through the orifice during 8.59 s, corresponding to a speed of 11.65 g/s.

Variants of Examples 1, 2 and 3

The volume of the liquid used for preparation of the granulate material may vary and, accordingly, the ratio between the volume of the liquid and the mass of the powder to be treated with the liquid varies.

In a first variant the liquid comprised 30% of the total amount of Arabic gum while the powder fraction comprised 70% of the total amount of Arabic gum. By using a total amount of 500 g of Arabic gum this means that 150 g of Arabic gum had to be dissolved in an appropriate amount of distilled water in order to obtain a 25% (w/v) solution. This corresponds to a volume of 600 ml.

Thus, during the wet granulation process, 600 ml of granulating liquid are sprayed on to the material to be granulated (powder mix). For example, 600 ml of a 25% (w/v) Arabic gum solution has been sprayed on to 350 g of Arabic gum powder, corresponding to a ratio of about 2:1.7 (ml/g).

In a further variant, the liquid contained 25% of the total amount of Arabic gum to be used, which means, with respect to a total amount of 500 g, 125 g of Arabic gum had to be dissolved in an appropriate amount of distilled water in order to achieve a 25% (w/v) solution. This corresponds to a total volume of the granulating liquid of 500 ml, which has been sprayed on to the material to be granulated, e.g. 375 g of Arabic gum powder, optionally mixed with an additive, corresponding to a ratio of about 1.3:1 (ml/g).

In another variant, the liquid comprised 20% of the total amount of Arabic gum to be dissolved in an appropriate amount of distilled water. While the total amount still is 500 g Arabic gum, 20% of Arabic gum correspond to 100 g of Arabic gum. The volume of the granulating liquid is accordingly 400 ml. Consequently, the ratio of liquid to powder was 400 ml per 00 g, i.e. 1:1 (ml/g).

In a further variant, only 5% of the total amount of Arabic gum to be used were dissolved in distilled water. This corresponds to 25 g of Arabic gum if a total amount of 500 g Arabic gum are used. Thus, the volume of the granulating liquid having an Arabic gum concentration of 25% (w/v) is 100 ml in this case. Consequently, 100 ml liquid have been sprayed on to, e.g. 475 g of Arabic gum powder and optionally further components, which corresponds to a ratio of 1:4.75 (ml/g).

All of the granulating liquids of the variant examples had a w/v concentration of 25% Arabic gum dissolved in distilled water. However, also a w/v ratio of around 20% up to around 30% solution is possible.

Variant 1 (ratio 1.7:1 liquid:powder) and variant 2 (ratio 1.3:1 liquid:powder) resulted in a very coarse grained agglomerate, clumping and poor solubility. Variant 3 (ratio 1:1 liquid:powder) and variant 4 (ratio 1:4.75 liquid:powder) resulted in less clumping and satisfying solubility.

Example 4: Granulate Material of Arabic Gum and Calcium Gluceptate, Comprising 8% (w/w) Arabic Gum A total amount of 47.76 g of Arabic gum has been used as matrix agent. 552 g of calcium gluceptate have been used as an effective agent.

The material to be granulated has been prepared by weighing of the calcium gluceptate into a proper vessel.

Arabic gum has been dissolved completely in an appropriate amount of distilled water to obtain a 25% (w/v) solution. The wet granulation process has been performed as described above.

Dissolution, Optical Analysis:

For optical analysis of the dissolution properties of the obtained granulate material, 10.0 g (8% (w/w) Arabic gum, 92% (w/w) calcium gluceptate) have been dissolved in 200 ml deionized water. Complete dissolution indicated by disappearance of turbidity has been observed after 24 seconds of manual stirring at room temperature.

Dissolution Property, Release of Ions:

In addition to the manual dissolution and optical analysis described above, the release of ions in the solution has been measured using Erweka type DT600 dissolution tester and Metrohm 856 Conductivity Module at room temperature. 11.20 g granulate have been added to 800 ml water to reach the desired mass concentration (w/w). The granulate material dissolved within the first few minutes.

It can be seen from FIG. 9 that a conductivity of about 2,000 mS/cm has been achieved after a few seconds. After reaching this level of conductivity, conductivity remained constant over the following period of measurement of about so minutes. This means: after the first increase of the conductivity the whole amount of 11.20 g of the granulate material has been dissolved in the water.

Flow Property:

Flow property has been analyzed as described above. It can be seen from Table 1 shown in FIG. 10 that granulate materiel according to Example 4 flows with an average speed of 11.61 g/s through an orifice of 1.5 cm. Flow properties have been measured three times. In a first measurement, 98.9 g of granulate material according to Example 4 needed 10.22 s for flowing through the orifice corresponds to a speed of 9.68 g/s. In a second measurement, 100.0 g of granulate material were flowing through the orifice during 10.38 s corresponding to a speed of 9.63 g/s through the orifice, while, in a third measurement, 99.9 g of granulate material were flowing through the orifice during 10.36 s, corresponding to a speed of 9.64 g/s.

Example 5a: Standard Powder of Arabic Gum

As a control, the solution properties and flow properties of a standard powder of Arabic gum (spray dried or dispersion dessicatum Ph.Eu.) have been analyzed. Such standard Arabic gum powders are available, e.g., from Sigma-Aldrich or Hansler.

Dissolution, Optical Analysis:

10 g of standard Arabic gum powder have been dissolved in 200 ml deionized water. There was no complete dissolution observed with manual stirring at room temperature over a time period of about 1 hour.

Flow Property:

Flow property has been analyzed as described above. However, the powder did not flow at all through the orifice as can be seen from FIG. 10.

Example 5b: Mixture of Standard Powder Arabic Gum and Calcium Gluceptate

As a further control, the 500 g of Arabic gum powder has been mixed with 129.1 g calcium gluceptate salt in an appropriate mixer without mixing and chopping blades to ensure mixture homogeneity as described above. The material corresponds to the prepared material to be granulated (powder mix) of Example 2. The product has been removed from the mixer and stored in a proper vessel. No further treatment by application of a liquid or within a fluid-bed granulator has been performed.

Dissolution, Optical Analysis:

12.6 g of the powder mixture (79.4% m/m Arabic gum, 20.6% m/m calcium gluceptate) have been dissolved in 200 ml deionized water. There was no complete dissolution observed with manual stirring at room temperature after about 1 hour.

Dissolution Property, Release of Ions:

In addition to the manual dissolution and optical analysis described above, the release of ions in the solution has been measured using Erweka type DT600 dissolution tester and Metrohm 856 Conductivity Module at room temperature as described above. 50.40 g powder mix have been added to 800 ml water to reach the desired mass concentration (w/w). The powder mix did not dissolve completely during a time period of about so minutes (FIG. 9).

It can be seen from FIG. 9 that conductivity increased continuously during the whole period of so minutes. In the end of the measurement conductivity has been about 2,000 mS/cm and, thus, far below the above 4,500 mS/cm of the corresponding granulate material of Example 2 that consists of the same components but is treated according to the invention. This means, that the powder mix of Example 5b was only partially dissolved during the experiment.

Flow Property:

Flow property was analyzed as described above. However, the powder did not flow at all through the orifice, as can be seen from FIG. 10.

Example 5c: A Mixture of Standard Powder Arabic Gum and Magnesium Lactate

The mixture of Arabic gum and magnesium lactate has been prepared by mixing the Arabic gum with Magnesium lactate in an appropriate mixer to ensure mixture homogeneity as described for Example 3. Afterwards, the product was removed from the mixer and stored in a proper vessel.

Dissolution, Optical Analysis:

12.0 g of the powder mixture (83.3% w/w Arabic gum, 16.7% w/w magnesium lactate) have been dissolved in 200 ml deionized water. There was no complete dissolution observable with manual stirring at room temperature after about 1 hour.

Dissolution Property, Release of Ions:

In addition to the manual dissolution and optical analysis described above, the release of ions in the solution has been measured using Erweka type DT600 dissolution tester and Metrohm 856 Conductivity Module at room temperature. 48.0 g powder mix have been added to 800 ml water to reach the desired mass concentration (w/w). The powder mix did not dissolve completely during a time period of about 30 minutes (FIG. 9).

It can be seen from FIG. 9 that conductivity increased continuously during the whole period of 30 minutes. In the end of the measurement, a conductivity of below 1,500 mS/cm has been observed, which is far below the nearly 3,000 mS/cm of the corresponding granulate material of Example 3. This means that the powder mix of Example 5c was only partially dissolved during the experiment.

Flow Property:

Flow property has been analyzed as described above. However, the powder did not flow at all through the orifice as can be seen from FIG. 10.

Example 6a: Granulate Material Containing Arabic Gum, Magnesium Lactate, Calcium Gluceptate and Zinc Gluconate Granulate material comprising more than one organic metal salt has been prepared. For the preparation of "Multi-batch 5/1" granulate material the following amounts of ingredients have been mixed as described above for preparing the material to be granulated: 10 g Arabic gum, 0.8 g magnesium lactate, 2.4 g calcium gluceptate, 20.9 mg zinc gluconate.

The granulating solution has been prepared by dissolving Arabic gum in distilled water to obtain a 25% (w/v) solution. The granulation process has been performed as described above. The obtained granulate material can be seen in FIG. 5. The particle size and particle size distribution of the granules making up the obtained granulate material as well as of the powder mix starting material are shown in FIG. 15.

Example 6b: Granulate Material Containing Arabic Gum, Magnesium Lactate, Calcium Gluceptate and Zinc Gluconate In Example 6b a variant of the multi-batch granulate material described in Example 6a has been prepared. For the preparation of the material to be granulated 10 g Arabic gum powder has been mixed with 1.81 g magnesium lactate, 4.1 g calcium gluceptate and 34.8 mg zinc gluconate as described above. The wet granulation process has been performed as described above. The obtained granulate material can be seen in FIG. 6. The particle size and particle size distribution of the granules making up the obtained granulate material as well as of the powder mix starting material are shown in FIG. 16.

The invention claimed is:

1. A wet granulation process preparing granules comprising contacting a material to be granulated with a granulating liquid, wherein the granulating liquid comprises Arabic gum and the concentration of Arabic gum in the granulating liquid is from about 5% to about 40% (w/v) and wherein the material to be granulated is Arabic gum or one or more metal salts where the metal is selected from the group consisting of potassium, sodium, lithium, calcium, magnesium, zinc, selenium, and iron, and wherein the counter ion of the metal salt is an organic counter ion selected from the group consisting of acetate, alginate, ascorbate, aspartate, amygdalate, benzoate, borogluconate, carbasalate, citrate, cyclamate, dinatriumtetralactate, dobesilate, ferro-phospholactate, folinate, formate, fumarate, glubionate, glucoheptonate, gluconate, glutamate, glycerophosphate, iopodate, ketoglutarate, lactate, lactogluconate, laevulinate, malate, methionate, orotate, oxalate, pangamate, pantothenate, phospholactate, phatalate, picrate, pidolate, propionate, resinate, saccharate (glucarate), saccharin, sorbate, and succinate; wherein the individual granules are porous; wherein the granules have a mean particle size of about 200 um to about 600 um; wherein the granules comprises pores, wherein the pore diameter is between about 5 um and about 150 um; wherein the shape of the granules is irregular.

2. The process according to claim 1, wherein the material to be granulated comprises Arabic gum, in an amount of at least 20% (w/w).

3. The process according to claim 1, wherein the granulating liquid is finely dispersed when contacted with the material to be granulated, by spraying nebulising the granulating liquid, wherein the wet granulation process is a fluidized bed granulation process.

4. The process according to claim 1 for increasing dissolution kinetics of the material to be granulated.

5. The process according to claim 2, wherein the Arabic gum is evenly distributed throughout the material to be granulated and the granulating liquid.

6. The process according to claim 1, wherein the material to be granulated does not comprise tannins, honey solution, microcellulose and/or tricalcium phosphate.

7. The process according to claim 1, wherein the material to be granulated comprises Arabic gum, in an amount of at least 50% (w/w).

8. The process according to claim 1, wherein the concentration of Arabic gum in the granulating liquid is from about 20% to about 30% (w/v).

9. The process according to claim 1, wherein the concentration of Arabic gum in the granulating liquid is 25% (w/v).

10. The process according to claim 1, wherein the material to be granulated does not include carbonate.

* * * * *